US010179212B2

(12) United States Patent
Stefansen et al.

(10) Patent No.: US 10,179,212 B2
(45) Date of Patent: Jan. 15, 2019

(54) INJECTION DEVICE HAVING NEEDLE SHIELD LOCKING

(71) Applicant: Novo Nordisk A/S, Bagsvaerd (DK)

(72) Inventors: Mads Schenstroem Stefansen, Copenhagen OE (DK); Soeren Kjellerup Hansen, Fjenneslev (DK); Bastian Gaardsvig Kjeldsen, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 240 days.

(21) Appl. No.: 15/317,475

(22) PCT Filed: Jun. 26, 2015

(86) PCT No.: PCT/EP2015/064622
§ 371 (c)(1),
(2) Date: Dec. 9, 2016

(87) PCT Pub. No.: WO2015/197867
PCT Pub. Date: Dec. 30, 2015

(65) Prior Publication Data

US 2017/0136192 A1 May 18, 2017

(30) Foreign Application Priority Data

Jun. 27, 2014 (EP) .................................... 14174800

(51) Int. Cl.
*A61M 5/32* (2006.01)
*A61M 5/20* (2006.01)
(Continued)

(52) U.S. Cl.
CPC ........ *A61M 5/3245* (2013.01); *A61M 5/2033* (2013.01); *A61M 5/2053* (2013.01);
(Continued)

(58) Field of Classification Search
CPC .............. A61M 5/2033; A61M 5/3202; A61M 2005/2013; A61M 2005/208;
(Continued)

(56) References Cited

U.S. PATENT DOCUMENTS

2007/0265568 A1* 11/2007 Tsals .................. A61M 5/2033 604/136
2014/0025006 A1* 1/2014 Takemoto ........... A61M 5/2033 604/110

FOREIGN PATENT DOCUMENTS

EP 2695630 A1 2/2014
WO 2006/052737 A1 5/2006
WO 2012/137803 A1 10/2012

* cited by examiner

*Primary Examiner* — Jason Flick
(74) *Attorney, Agent, or Firm* — Wesley Nicolas

(57) ABSTRACT

An injection device for expelling a dose of drug from a held cartridge (600) is described. A needle shield (350, 380) is axially movable relative to a base (200, 220, 230) between a proximal collapsed position and a distal extended position. A needle shield lock comprises a deflectable lock element (392) operable to prevent the needle shield (350, 380) from being moved towards the proximal collapsed position. A lock activator (402) associated with a plunger (310, 400) exerts an activation force on the deflectable lock element when the plunger assumes a final position. A biasing means (403) is arranged to act between the lock activator (402) and the deflectable lock element (392), the biasing means (403) being configured to resiliency transfer the activation force from the lock activator (402) to the deflectable lock element (392) to enable the needle shield (350, 380) to become locked in the distal extended position but only when the plunger (310, 400) assumes the final position.

17 Claims, 13 Drawing Sheets

Figure 1A:
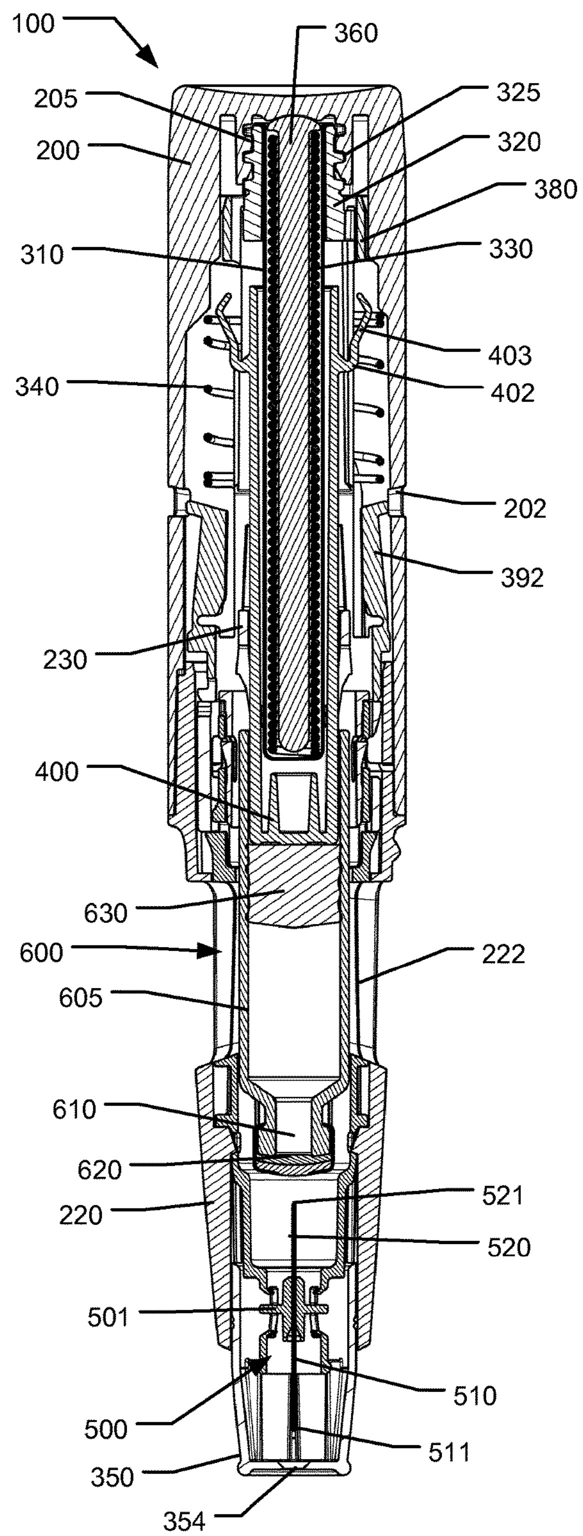

(51) Int. Cl.
*A61M 5/50* (2006.01)
*A61M 5/315* (2006.01)

(52) U.S. Cl.
CPC ...... *A61M 5/31515* (2013.01); *A61M 5/3202* (2013.01); *A61M 5/326* (2013.01); *A61M 5/50* (2013.01); *A61M 2005/208* (2013.01); *A61M 2005/2013* (2013.01); *A61M 2005/3247* (2013.01); *A61M 2005/3267* (2013.01)

(58) Field of Classification Search
CPC .. A61M 2005/3247; A61M 2005/3267; A61M 5/2053; A61M 5/31515; A61M 5/3245; A61M 5/326; A61M 5/50
USPC .......................................................... 604/198
See application file for complete search history.

INJECTION DEVICE HAVING NEEDLE SHIELD LOCKING

CROSS-REFERENCE TO RELATED APPLICATIONS

This application is a 35 U.S.C. § 371 National Stage application of International Application PCT/EP2015/064622 (published as WO2015/197867), filed Jun. 26, 2015, which claims priority to European Patent Application 14174800.4, filed Jun. 27, 2014; the contents of which are incorporated herein by reference.

FIELD OF THE INVENTION

The present invention relates to injection devices for injecting a medicament. In particular the present invention relates to injection devices having a needle shield to shield a held needle and means for locking the needle shield in a shielded state after use.

BACKGROUND OF THE INVENTION

In relation to some diseases patients must inject a medicament on a regular basis such as once weekly, once daily or even a plurality of times each day. In order to help patients overcome fear of needles, fully automatic injection devices have been developed with the aim of making the use of the injection device as simple and safe as possible. Such devices are typically designed such that a user shall position the injection device onto the injection site and activate the device. Such activation causes the device to insert a needle into the skin, eject a dose of the medicament and subsequently move the needle into a shielded position.

In injection devices, and in particular in auto injector devices with an integrated and shielded needle, it is desirable that the needle shield is locked after use. Some prior art devices include a locking feature where the locking feature is activated immediately after the needle shield is deflected for an injection whereafter, when the needle shield is extended into its shielding position, the lock is effectuated. This is sometimes a disadvantage due to the nature of auto injectors where a powerful pre-tensioned spring is released when the device is activated. Some patients may become surprised by the activation sound and/or reaction force and removes the device from the skin. In injectors where the needle shield locks when the device is prematurely removed from the skin the patient is unable to receive the intended dose.

WO 2012/137803 discloses an autoinjector wherein a needle protector is locked in a position shielding a needle but only after a dose has been finalised and the plunger has reached a final position. However, the disclosed device is associated with drawbacks having regard to movement of the protector which may tend to become jammed during extraction of the protector relative to the housing. Also, the robustness of the locking mechanism of the needle protector is not optimal. Furthermore, the locking of the protector occurs via further components making device unnecessary complex.

Having regard to the above-identified prior art devices, it is an object of the present invention to provide an injection device that is improved having regard to locking of the needle shield subsequent to performing an injection.

Yet additional further objects of the invention are to provide measures for obtaining devices having a superior performance and, at the same time, enabling manufacture at a reduced cost.

BRIEF DESCRIPTION OF THE INVENTION

In a first aspect the present invention relates to an injection device for expelling a dose of drug from a held cartridge, the injection device comprising:

a base, a drug cartridge arranged relative to the base, the cartridge comprising:

a) an elongated body having a distal end and a proximal end and defining a central longitudinal axis, the body having a distally arranged outlet adapted for connection to a needle, and b) a piston accommodated in the body, the piston configured for being driven axially in the distal direction to expel a dose of a drug through the outlet, a plunger adapted for cooperation with the piston and driveable towards a final position, and a needle shield axially movable relative to the base between a proximal collapsed position and a distal extended position, wherein the injection device defines a needle shield lock so configured that, when the plunger assumes the final position and when the needle shield assumes the distal extended position, the needle shield lock prevents the needle shield from being moved towards the proximal collapsed position, wherein the needle shield lock comprises a deflectable lock element movable from a passive configuration wherein the deflectable lock element does not prevent the needle shield from being moved towards the proximal collapsed position and into an active configuration wherein the deflectable lock element prevents the needle shield from being moved towards the proximal collapsed position, wherein the plunger comprises a lock activator configured for operating the deflectable lock element and being so configured that, when the plunger assumes the final position, the lock activator exerts an activation force on the deflectable lock element for urging the deflectable lock element towards the active configuration, and wherein a biasing means is arranged to act between the lock activator and the deflectable lock element, the biasing means being configured to resiliently transfer the activation force from the lock activator to the deflectable lock element for causing the deflectable lock element to be moved into its active configuration as the needle shield is moved into its distal extended position.

Due to the biasing means resiliently transfers the activation force from the lock activator to the deflectable lock element this enables constructional freedom in designing the needle shield lock to obtain a robust shield lock function. The resiliency of the biasing means allow use of rigid or substantial rigid lock components to be used that assume well defined positions in the passive configuration as well as in the active configuration. In addition, the needle shield lock can be moved from its passive configuration to its active configuration while exhibiting low friction between the components when they move relative to each other. As a further advantage, the construction enable compact design of the needle shield locking function since it requires only small dimensions in the direction of movement for the deflectable lock element from its passive configuration to its active configuration.

The needle shield may be configured for movement along the central longitudinal axis. When the needle shield assumes the distal extended position the needle of the device is protected by the needle shield preventing a user from touching the needle. The injection device may accommodate a needle that is fixedly mounted relative to the base. In such embodiments when the needle shield assumes the collapsed proximal position, a front part of the needle protrudes through the needle shield. In other embodiments, the injection device may incorporate a needle that is axially movable relative to the base and wherein the needle is only brought into a distal position upon dose administration. For such embodiments, dependent on the particular design of the device, when the needle shield assumes the collapsed proximal position the front end of the needle will or will not initially protrude through the needle shield. However, upon triggering of the device the needle will either protrude or be brought to protrude through the needle shield enabling needle penetration at an injection site.

The device may be so configured that when the needle shield assumes its extended distal position while the plunger assumes one of a predefined range of positions proximally located relative to the final position, the lock activator does not exert an activation force for urging the deflectable lock element into the active configuration.

In particular embodiments, at least one of the lock activator and the deflectable lock element comprise a biasing means for exerting said activation force, the biasing means being configured for causing the deflectable lock element to be moved into its active configuration as the needle shield is moved into its distal extended position. In other embodiments both the lock activator and the deflectable lock element comprise a biasing means.

The deflectable lock element may be arranged to be moved in a first direction when moving from the passive configuration (e.g. a passive position) to the active configuration (e.g an active position) and wherein the biasing means is configured for providing resiliency along the first direction for resiliently transferring said activation force from the lock activator to the deflectable lock element. Said first direction may be a radially outwards direction or a radially inwards direction. In other embodiments, said first direction may be a circumferential direction.

The deflectable lock element may assume the passive configuration when not being exerted to said activation force by the lock activator. However, when the plunger assumes the final position, the lock activator exerts an activation force on the deflectable lock element in response to the needle shield being moved into its distal extended position and the deflectable lock element is only moved into its active configuration in the course of the needle shield enters into its distal extended position. The deflectable lock element is prevented from entering into the active position when the needle shield assumes a predetermined range of position other than the distal extended position.

The base may define a retaining or locking geometry for cooperating with the deflectable lock element to prevent the needle shield from being moved in the proximal direction when the deflectable lock element assumes its active configuration. In some embodiments the deflectable lock element engages directly with the retaining or locking geometry when the deflectable lock element assumes the active position. In addition, the deflectable lock element may engage a component of the base which component is provided as a rigid component either as a part defining an outer housing of the device or as a part that is mounted immovably relative to an outer housing. A superior robustness for the shield lock may thus be enabled.

The deflectable lock element may be configured to lock relative to the base when the deflectable lock element assumes the active configuration. The base may define a locking geometry configured for cooperation with the deflectable lock element to maintain the deflectable lock element axially locked relative to the base when the deflectable lock element assumes the active position In some embodiments, the base comprises a retaining geometry having a distally facing surface configured for cooperating with a proximally facing surface of the deflectable lock element to prevent the needle shield from moving in the proximal direction when the deflectable lock element assumes the active position.

The retaining geometry of the base may be configured as a recessed area and wherein a sliding surface is arranged proximally relative to the recessed area enabling the deflectable lock element to slide relative to the sliding surface when the deflectable element is not assuming its active position.

The deflectable lock element may be defined as or comprise a deflectable arm wherein at least a part of the deflectable arm is configured for moving radially from the passive to the active position. An end portion of the deflectable locking element may be configured to engage with a retaining geometry of the base.

In exemplary embodiments, the deflectable lock element defines an elongated rigid beam having a proximal end that is configured for cooperating with the locking geometry and having a distal end that connects to the needle shield by means of a hinge so that the proximal end of the elongated rigid beam is movable in a radial direction from the passive position to the active position.

The hinge may be formed as a living hinge. In some embodiments, the rigid beam is formed in one piece with the needle shield or in one piece with a component rigidly connected with the needle shield.

In embodiments where the deflectable lock element forms an elongated rigid beam, when the deflectable lock element assumes the active position the elongated rigid beam extends along an axis having an inclination relative to the central longitudinal axis being less than 30 degrees, more preferably less than 20 degrees, and most preferably less than 10 degrees. Hence, when the needle shield is locked subsequently to withdrawing the injection device from the injection site, large forces exerted in proximal direction onto the needle shield will largely be transferred to forces acting on the base, primarily acting in the proximal direction.

The proximal end of the elongated rigid beam may comprise a proximally facing surface configured to cooperate with a distally facing surface of the retaining or locking geometry. The proximally facing surface and/or the distally facing surface may be formed inclined with respect to a normal to the central longitudinal axis so that the deflectable lock element, when assuming the active position, is increasingly urged in said radial direction upon increasing force acting in the proximal direction on the needle shield.

In exemplary embodiments, a plurality of deflectable locking elements is arranged, each deflectable locking element being configured for cooperating or engaging with a respective retaining or locking element of the base. In accordance herewith, the lock activator may be configured for exerting an activation force on each of the deflectable locking element. The plurality of deflectable locking elements may be arranged at the same axial position. However, said plurality of locking elements need not be arranged at the same axial position but may be distributed along the axis. A respective biasing means may be arranged for each deflectable element to resiliently transfer an activation force from the lock activator.

A needle shield spring may be arranged to act upon the needle shield with a biasing force tending to move the needle shield distally, i.e. towards the extended position. The needle shield shields a held needle when the needle shield assumes its distal extended position. A held needle may be arranged at a fixed axial location relative to the base throughout operation of the device, or may alternatively be arranged for initially moving distally when initiating an injection.

In some embodiments, the injection device forms a device adapted for being manually operated by a user manually pushing forward a piston of a held cartridge. In other embodiments, the injection device forms an autoinjector. Such autoinjector may comprise an actuator for providing a force arranged to act on the plunger. The actuator is triggerable to drive the plunger and thus the piston of the cartridge distally. The actuator may be configured for being triggered by pushing an activation button. In alternative embodiments, the actuator may be configured for being triggered by moving the needle shield in proximal direction.

The biasing means may in exemplary embodiments be arranged for being moved axially with the plunger. The biasing means may in some embodiments be formed integrally with the lock activator.

In alternative embodiments, the biasing means may be moved axially with the needle shield, e.g. such as when the biasing means are fixedly attached to the needle shield or formed by a component of the needle shield. In still other embodiments, the biasing means may be arranged at a fixed axial position relative to the base.

In still other exemplary embodiments, the deflectable lock element may be configured for being moved in a circumferential direction between a passive (non-locked) position and into an active (locked) position where the deflectable lock element locks relative to the housing of the device. In such embodiments, the lock activator may be configured so that it exerts a torsional activation force on the deflectable lock element subject to the plunger having reached its end of dose position. In such embodiments, biasing means may be arranged between the lock activator and the deflectable lock element and configured to provide resiliency in the circumferential direction for resiliently transferring a torsional activation force from the lock activator towards the deflectable lock element. This causes the deflectable lock element to be moved circumferentially into its active position as the needle shield is moved into its distal extended position.

Still further beneficial embodiments are defined by the subject matter disclosed below in relation to the second aspect of the present invention.

In a second aspect the present invention relates to an autoinjector for expelling a single dose of drug from a held cartridge, comprising:

a base, a drug cartridge arranged relative to the base, the cartridge comprising:

a) an elongated body having a distal end and a proximal end and defining a central longitudinal axis, the body having a distally arranged outlet adapted for connection to a needle, and b) a piston accommodated in the body, the piston configured for being driven axially in the distal direction to expel a dose of a drug through the outlet, a plunger adapted for cooperation with the piston, an actuator for providing a force and arranged to act on the plunger to drive the piston distally, a needle shield axially movable relative to the base between an extended position and a collapsed position, wherein the autoinjector defines a trigger lock configured for releasably maintaining the plunger in an initial axial position against the force of the actuator, the trigger lock being operated by the needle shield.

In some embodiments the trigger lock may define a configuration wherein the plunger associates with a plunger thread component and the base defines a base thread component adapted for operatively coupling with the plunger thread component, wherein prior to activation, a) the plunger thread component is operatively coupled with the base thread component and b) the trigger lock acts to prevent relative rotation between the plunger thread component and the base thread component, thereby maintaining the plunger in the initial axial position, and wherein the trigger lock is so configured that, upon the needle shield being moved towards the collapsed position, the trigger lock is released enabling relative rotation between the plunger thread component and the base causing release of the plunger from the initial axial position and expelling the dose of the drug.

The device may thus define a needle shield triggered expelling assembly where the actuator, such as a prestressed actuating spring, is actuated for releasing axial movement of the plunger by a movement of the needle shield relative to the base. The needle shield may be configured for moving along an axis identical or running in parallel to the central longitudinal axis of a held cartridge. According to one aspect, as the energy accumulated in the actuator is not changed when the needle shield is moved axially from the extended position to the collapsed position, the force exerted on the needle shield for performing this movement does not induce a movement of the plunger against the force provided by the actuator, such as a prestressed actuating spring. Hence, in particular for autoinjectors having an actuator configured for exerting a large force on the plunger, such as autoinjectors for expelling high-viscosity liquids or autoinjectors configured for use with thin injection needles, the movement of the needle shield is largely unhindered by the force provided by the actuator.

The autoinjector may be so configured that, prior to release of the trigger lock while operatively coupling between the base thread component and the plunger thread component is maintained, the force applied by the actuator transfers into a force having a force component that acts to rotate the base thread component and the plunger thread component relative to each other. Apart from forces exerted by a possible needle shield spring, only frictional forces attributable to moving needle shield components needs to be overcome when moving the needle shield for triggering the expelling assembly.

The trigger lock may be configured to include engaging first and second components having cooperating geometries that prior to activation engage to maintain the lock and which upon activation disengage and where the disengagement does not incorporate deformation of the cooperating geometries.

The cartridge body may define a proximally facing rear surface. The distally arranged outlet of the cartridge may comprise a pierceable septum adapted to be pierced by the rear needle of a needle unit having both a front needle extending in the distal direction and a rear needle extending in the proximal direction. In alternative configurations, the cartridge body outlet portion includes an injection needle fixedly attached relative to the cartridge body.

In some embodiments, the base forms a housing of the device. The autoinjector may accommodate a needle that is fixedly mounted relative to the base.

In some embodiments, the front needle is configured to be manually operable relative to the needle shield such that when the needle shield is held against an injection site, manual operation of the front needle relative to the needle shield or vice versa causes manual penetration of the front needle into the injection site and causes subsequent release of the trigger lock.

By configuring the device so that a pushing force exerted manually on a part of the device is transferred to a manual force acting on the needle for manual penetration of the front needle into the injection site, the user gains improved control of the insertion of the injection needle. At the same time, by using this configuration the needle is hidden from the user during an administration. By providing an improved control of the needle insertion procedure a potential uneasiness for the user can be alleviated. The first part of the activation movement moves the needle forward relative to the needle shield to insert the needle in the user's skin. The second part of the movement activates the expelling assembly. In particular embodiments, this allows the user to manually insert the front tip of the needle before activating the device and an administration may be stopped in time should the user wish to abort the operation.

Relative rotational movement between the plunger thread component and the base thread component is performed around a first rotational axis. In some embodiments the first rotational axis is arranged coaxially with respect to the central longitudinal axis of the body of the cartridge. In other embodiments, the first rotational axis and the central longitudinal axis are arranged non-coaxially with respect to each other.

In the context of the present disclosure, when referring to "a base thread component", "a plunger thread component", and "a base thread component being adapted for operatively coupling with the plunger thread component" this shall be so construed that when the plunger thread component is operatively coupled with the base thread component the relative movement between the plunger and the base is provided by means of a helical guiding movement. The helical guiding movement may be provided by either a direct engagement between the plunger and the base or by an indirect coupling via one or more further components arranged between the base and the plunger. Non-limiting examples of a helical guiding movement includes a threaded coupling and a track and track follower coupling. A threaded coupling may be provided by means of co-operating screw threads having a constant lead along the first rotational axis or a variable lead along the first rotational axis. A threaded component may be provided by means of a continuous threaded section or by means of a plurality of thread segments. A track and track follower coupling may define a track having a constant pitch relative to said first rotational axis or a track having a varying pitch along the first rotational axis.

When the helical guiding movement is provided by a threaded coupling, the threaded coupling may be formed as a non-self-locking threaded coupling.

The plunger thread component may be provided as an outer thread component extending radially outwards from the plunger and configured to engage an inner thread component provided by the base thread component. Alternatively, the plunger thread component may be provided as an inner thread component extending radially inwards from a side surface portion of an axial bore of the plunger configured to engage an outer thread component provided by the base thread component.

The needle may incorporate a sterility barrier for the front needle. In applications where a rear needle is present, a sterility barrier for the rear needle or for both the front needle and rear needle may be incorporated. In some embodiments, the respective sterility barrier may be formed as a flexible cover or sheath configured as a closed cavity for accommodating the needle, i.e. the front needle or the rear needle. During operation of the device the flexible cover or sheath is configured for being penetrated by the needle.

The injection device may comprise an actuator in the form of a stored energy source coupled to the plunger and configured for driving the plunger upon release of the trigger lock. Non-limiting examples of a stored energy source include a spring element, such as a pre-strained spring, a compressed gas etc., wherein the stored energy may be accumulated during manufacture of the autoinjector. In other forms, the energy source is configured to become charged during an initial operation of the device prior to activation of the injection mechanism. The stored energy source stores sufficient energy to operate the autoinjector for expelling the total amount of drug that is intended to be expelled from a held cartridge, and, optionally, surplus energy for driving the cartridge forward for coupling to a rear needle and/or for driving the needle shield for a needle shielding operation.

In particular forms, the actuator is provided as a helical compression spring that exerts an axial force on the plunger. In alternative forms, the helical compression spring is configured to additionally exert a torque acting to rotate the plunger thread component and the base thread component relative to each other.

The plunger may include a drive ram. Further, the plunger may include a spacer member positioned between the drive ram and the piston of the held cartridge. The spacer member is mounted for axial displacement but may be prevented from performing rotational movements relative to the base. In some embodiments of the autoinjector the actuating spring is a helical compression spring arranged internally in a longitudinal bore of the drive ram. The drive ram may be made from a metal alloy, such as stainless steel. Alternatively, the drive ram may be made from a plastic material.

In some embodiments the autoinjector may include a needle shield spring which is associated with the needle shield and the needle to urge the front needle into its shielded state or to urge the needle shield into the state where the front needle is shielded. In particular embodiments the needle shield spring is an element separate from the actuator or the actuating spring. Exemplary non-limiting embodiments of a needle shield spring include springs such as a helical spring acting in compression mode and/or torsion mode, a leaf spring, a plastic spring or a plastic material spring element formed separately or integrally with other components of the autoinjector.

In some embodiments of the autoinjector, the trigger lock includes a first lock element that is axially movable as the needle shield moves from the extended position towards the collapsed position, wherein the first lock element and the plunger thread component define respective cooperating lock geometries configured to, prior to activation, maintain a rotational lock or retainment between the plunger thread component and the base thread component, the cooperating lock geometries being adapted to unlock or release retainment to enable free rotation between the plunger thread component and base thread component upon the needle shield being moved towards the collapsed position.

The first lock element may be formed integrally with the needle shield, as part of a needle shield sub-assembly or alternatively as a component separate from the needle shield but being operated by movement of the needle shield.

In particular embodiments of the autoinjector the first lock element is prevented from rotating relative to the base. The first lock element and the plunger thread component define respective cooperating lock or retainment geometries configured to, prior to activation, maintain a rotational lock or retainment between the plunger thread component and the first lock element, the cooperating lock geometries being adapted to unlock to enable free rotation between the plunger thread component and the first lock element upon the needle shield being moved towards the collapsed position.

In alternative embodiments the first lock element is allowed to rotate relative to the base when the needle shield has been pressed into its collapsed position but is prevented from rotating relative to the base when the needle shield is in the extended position. The first lock element and the plunger thread component define respective cooperating geometries configured to prevent or allow only limited relative rotation but allowing axial displacement.

It is to be noted that, in accordance with one aspect of the invention, the trigger lock needs only to remain enabled, that is to remain in locking mode, in the initial storage state, i.e. prior to activation of the expelling assembly. After activation of the expelling assembly the trigger lock is not required to enter into locking mode again, i.e. the lock elements need not prevent or limit relative rotation between the plunger thread component and the base thread component as the needle shield is returned to its extended position.

In some embodiments of the autoinjector the base thread component is fixedly disposed relative to the base, such as by being formed integrally with the base. When the base defines the housing or a section of the housing, the base thread component is thus axially and rotationally fixed relative to the housing.

In some embodiments the first lock element defines a first lock feature and the plunger thread component defines a cooperating lock feature, wherein one of the first lock feature and the cooperating lock feature defines an axial track and wherein the other of the first lock feature and the cooperating lock feature defines a track follower. In such embodiment the axial track may be formed as a track that extends in a direction parallel with the first rotational axis. Hence, when the needle shield is moved from the extended position towards the collapsed position, the trigger lock is released without inducing a relative rotation between the first lock element and the plunger thread component. Only subsequent to release of the trigger lock, i.e. when the track follower disengages the track, is rotation between the first lock element and the plunger thread component enabled. Thereafter rotational movement between the plunger thread component and the base thread component is induced by the force exerted by the actuator due to the operative coupling of the base thread component and the plunger thread component.

In other embodiments, instead of said axial track extending in a direction parallel with the first rotational axis, the axial extending track may be formed to extend at an angle with respect to the first rotational axis, such as less than 20 degrees, alternatively less than 15 degrees, alternatively less than 10 degrees, and still alternatively less than 5 degrees. Such slightly angled axially extending track would in particular applications be acceptable as only a limited rotation between the plunger thread component and the base thread component would be induced during axial displacement of the needle shield. Said limited rotation may be formed to provide an initial reluctance against proximal movement of the needle shield enabling a rapid needle insertion into the injection site.

In other alternative embodiments of the autoinjector, wherein the base forms part of or defines a housing of the autoinjector, the base thread component is defined by a rotatable component that is axially fixed but rotatably mounted relative to the base. The trigger lock includes a first lock element that is axially movable as the needle shield moves from the extended position towards the collapsed position. The first lock element and the rotatable component define respective cooperating lock geometries configured to, prior to activation, maintain a rotational lock between the rotatable component and the base, the cooperating lock geometries being adapted to unlock to enable rotation between the rotatable component and the base upon the needle shield being moved towards the collapsed position.

The first lock element may be prevented from rotating relative to the base. The first lock element and the rotatable component define respective cooperating lock geometries configured to, prior to activation, maintain a rotational lock or retainment between the rotatable component and the first lock element, the cooperating lock geometries being adapted to unlock or release said retainment to enable free rotation between the rotatable component and the first lock element upon the needle shield being moved towards the collapsed position. In such embodiments the plunger thread component may be prevented from rotating relative to the base. The plunger may be mounted non-rotationally relative to the base and the plunger thread component may be fixedly disposed on the plunger.

In some embodiments of the autoinjector the plunger thread component is only operatively coupled with the base thread component during an initial first axial displacement of the plunger whereas, in a second axial displacement, the plunger thread component is released from being operatively coupled with the base thread component allowing the plunger to subsequently continue axial displacement.

Subsequent to axial release of the plunger, the end of stroke position of the plunger may be provided by a pre-determined axial stop position of the plunger relative to the proximally facing rear surface of the cartridge. The autoinjector may be so configured that a stop geometry of the plunger directly engages the proximally facing rear surface of the cartridge. Alternatively, one or more intermediary components may be positioned between the plunger and the proximally facing rear surface of the cartridge to provide said pre-determined axial stop position of the plunger relative to the proximally facing rear surface of the cartridge.

In some embodiments of the autoinjector the plunger thread component comprises a geometry having a radial dimension, such as a diameter, that is larger than the internal diameter of a cylindrical section of the cartridge. In particular for autoinjectors having an actuator that stores a large amount of energy, the large dimensions of the plunger thread component enable a robust design that offers non-problematic long-term storage, even in situations where one or both of the thread components are made from a non-metallic material and where the actuator during long-term storage is kept in a pre-tensed state.

In particular embodiments, where the housing of the autoinjector has a total length of dimension L, the base thread component may be arranged to extend from the proximal end of the housing. The base thread component may be arranged to extend from the proximal end of the housing by less than 30% of L, alternatively less than 20% of L, alternatively less than 10% of L, and still alternatively less than 5% of L.

In particular embodiments, the plunger thread component may dimensioned to extend from the proximal end of the plunger in the distal direction along the plunger by a length corresponding to less than 75% of the entire plunger length, alternatively by a length corresponding to less than 50% of the entire plunger length, alternatively by a length corresponding to less than 25% of the entire plunger length, and still alternatively by a length corresponding to less than 15% of the entire plunger length.

In some embodiments of the autoinjector the plunger thread component is located at the proximal end of the plunger. The plunger and the plunger thread may be formed as a unitary component. In other embodiments the plunger thread component may be formed as a release nut arranged at a fixed axial location on the plunger. The release nut may be freely rotatable relative to the plunger. In such embodiments, the plunger may be so configured that it does not rotate relative to the base, e.g. by being rotationally locked relative to the base.

In some embodiments of the autoinjector, the device irreplaceably accommodates a cartridge within the base so that the cartridge cannot be removed from the device without the use of tools. In such embodiments, the autoinjector forms a disposable device.

In some embodiments of the autoinjector, the force acting for causing rotation between the plunger thread component and the base thread component for releasing the plunger from the initial axial position is at least partly exerted by the actuator. In particular embodiments, the force acting for causing rotation between the plunger thread component and the base thread component for releasing the plunger from the initial axial position is exclusively exerted by the actuator.

In some embodiments, an externally applied force on the needle shield for causing the needle shield to be moved into the collapsed position is not transmitted into a force component acting to cause rotation between the plunger thread component and the base thread component for releasing the plunger from the initial axial position. In still other embodiments, an externally applied force on the needle shield for causing the needle shield to be moved into the collapsed position is transmitted into a force component acting to cause rotation between the plunger thread component and the base thread component so as to cause release of the plunger from the initial axial position.

In embodiments incorporating a cartridge and a separate needle unit, the cartridge and the needle unit may be initially held in a configuration where the cartridge and the needle unit are separated by a distance. The actuator may be capable, upon release of the trigger lock, to cause the cartridge and the rear needle to enter into the state where the cartridge septum is pierced by the rear needle and subsequently to cause the plunger to move to dispense the medicament through the needle.

The injection device may incorporate an activator which is mechanically associated with the needle so that when the activator and the needle shield is moved relative to each other it causes the front needle and the needle shield to move relative to each other. In some embodiments the needle substantially follows movement of the activator as the activator moves relative to the needle shield. In particular embodiments, the needle is attached to the activator in a way preventing relative axial movements between the activator and the needle.

In some embodiments the activator is configured to define a housing section which at least partly accommodates the cartridge and where the housing section is adapted to be gripped by the hand of the user. In such embodiment, the activator may be coupled to the needle to transfer a force from the activator to the needle when the activator is moved relative to the needle shield.

As used herein, the term “medicament” is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

Figure 1B:
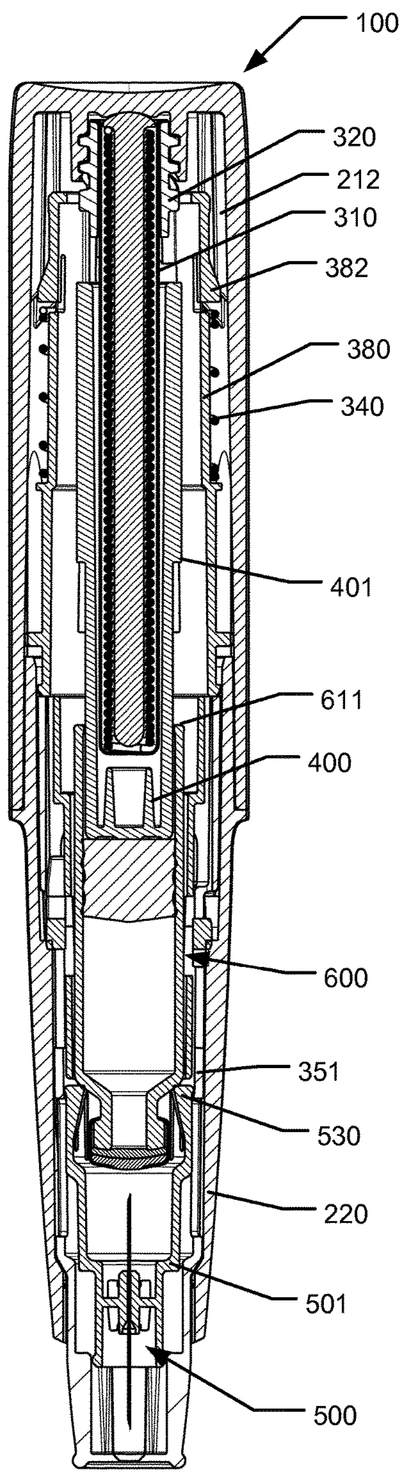
Figure 1C:
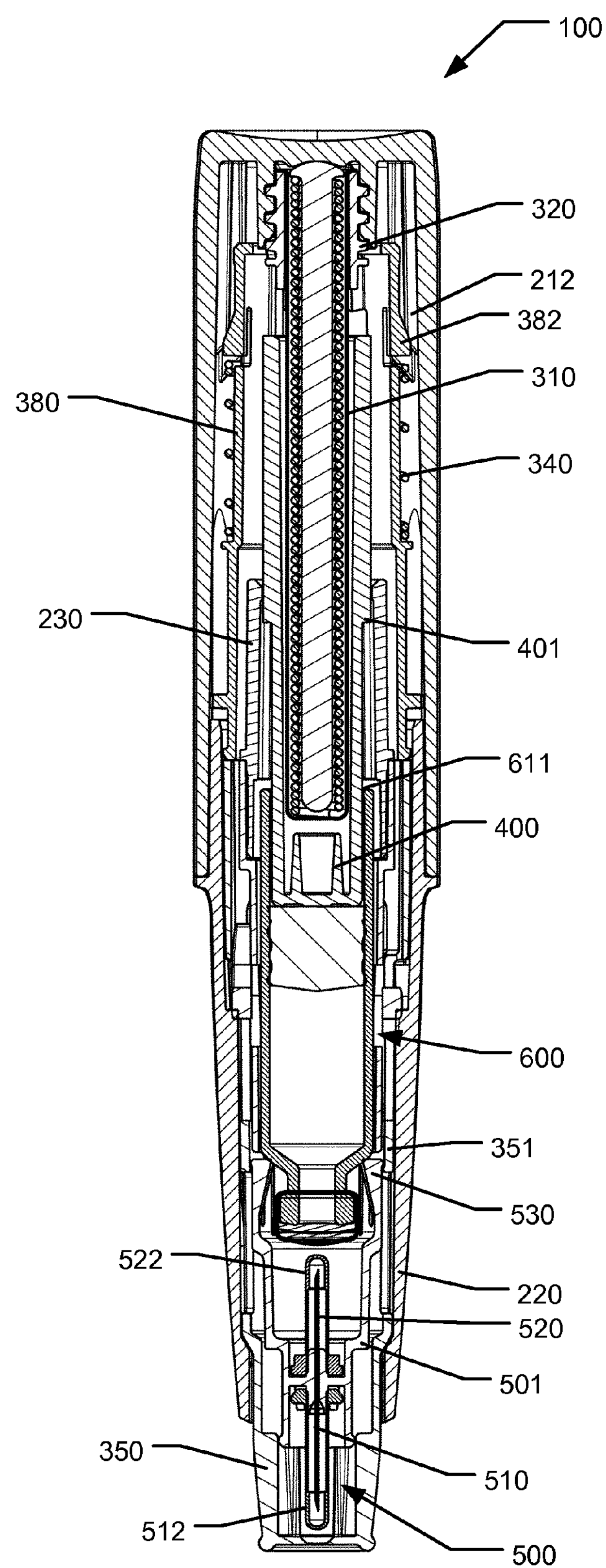
Figure 2A:
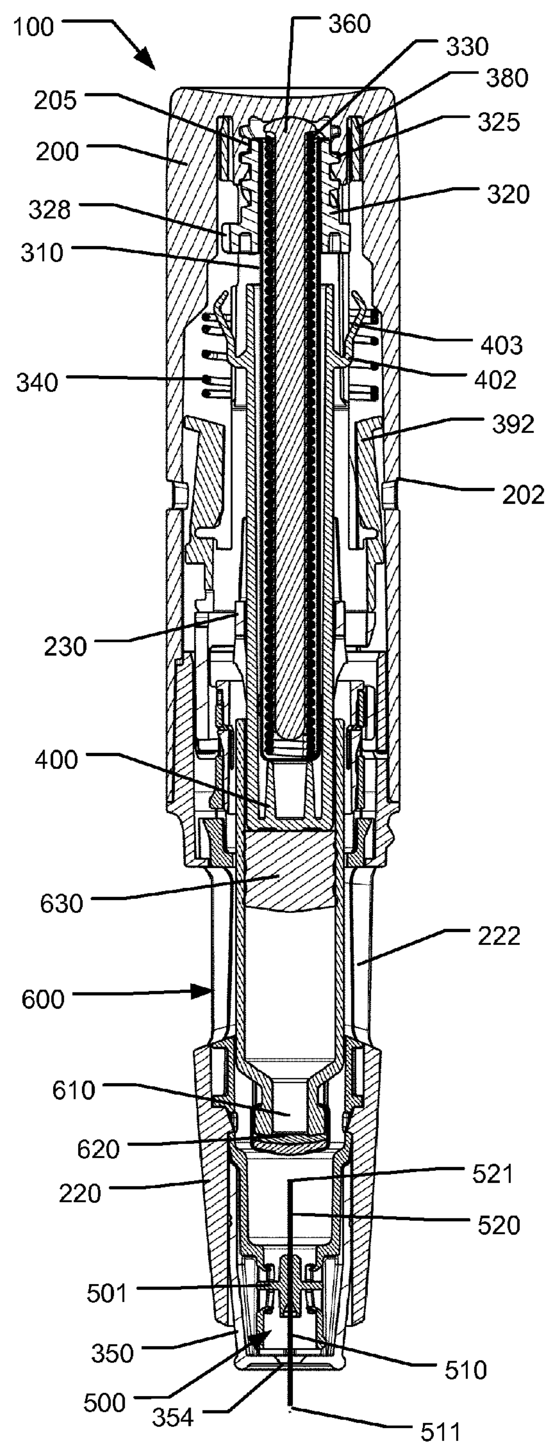
Figure 2B:
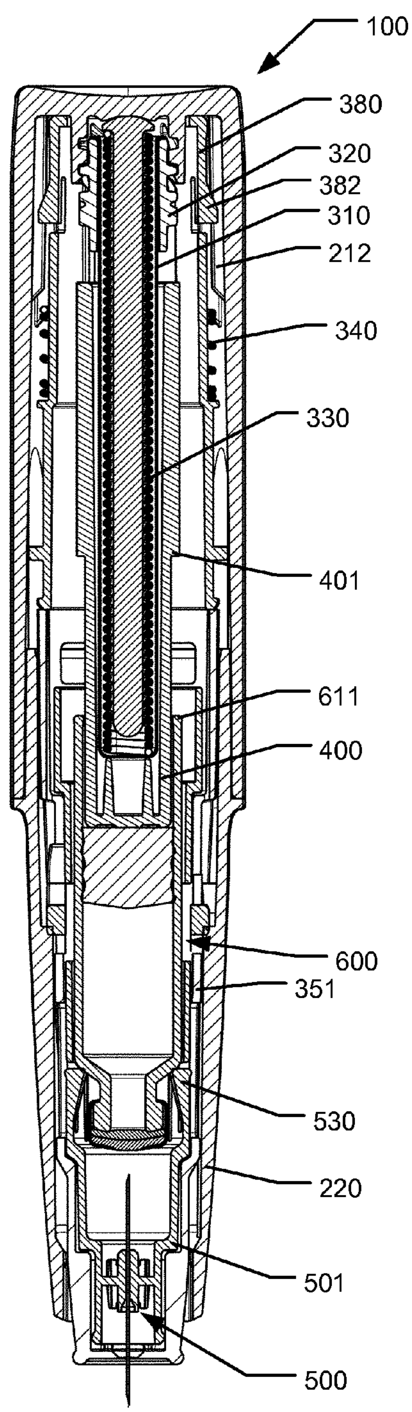
Figure 2C:
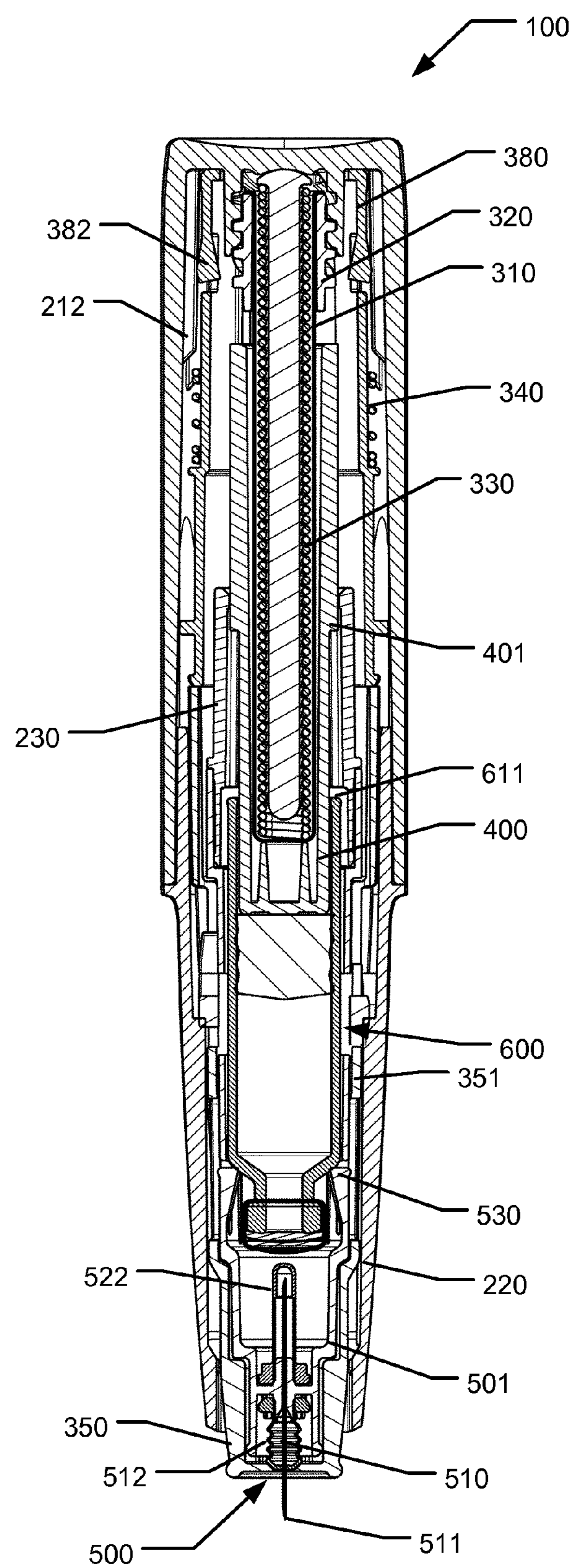
Figure 3A:
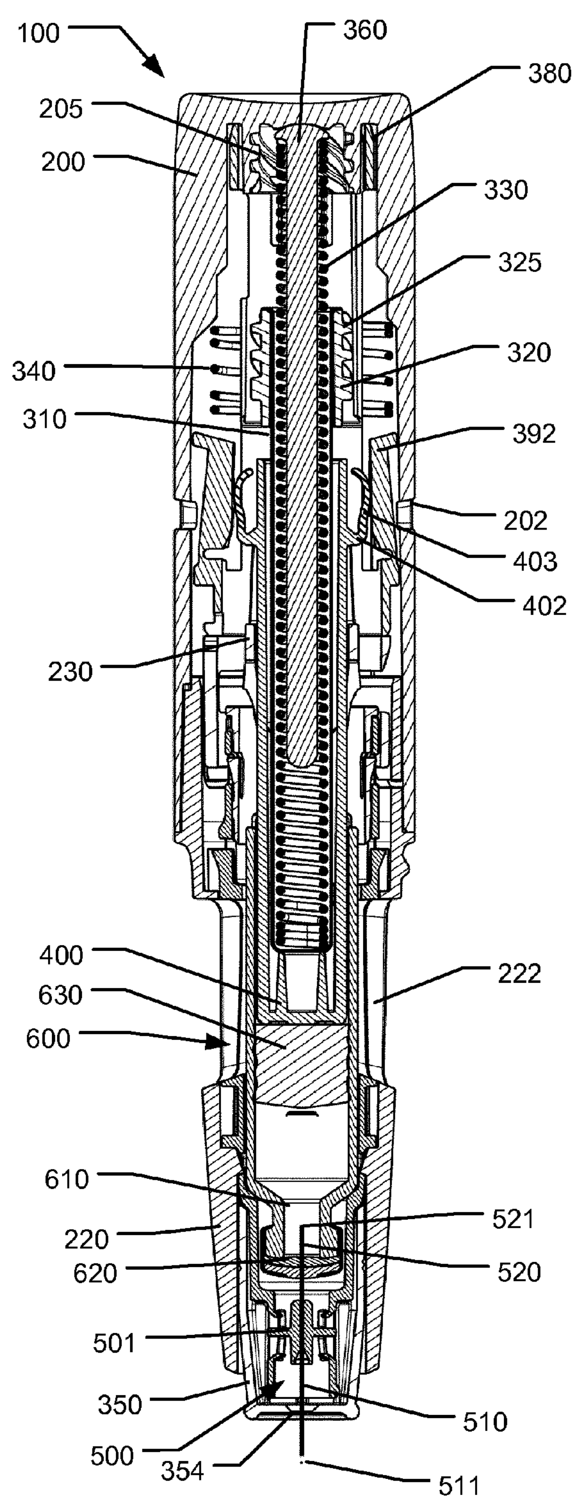
Figure 3B:
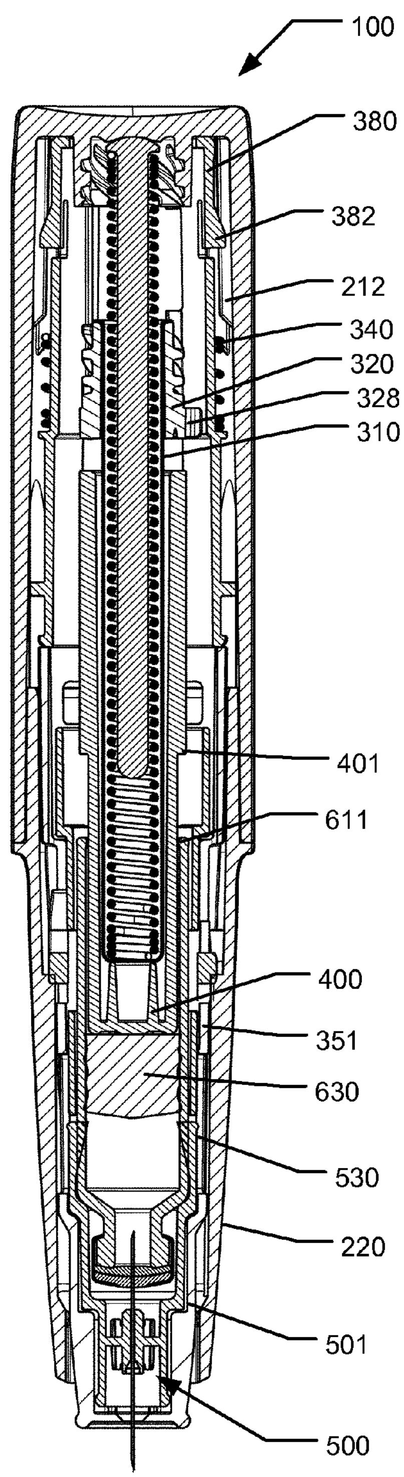
Figure 3C:
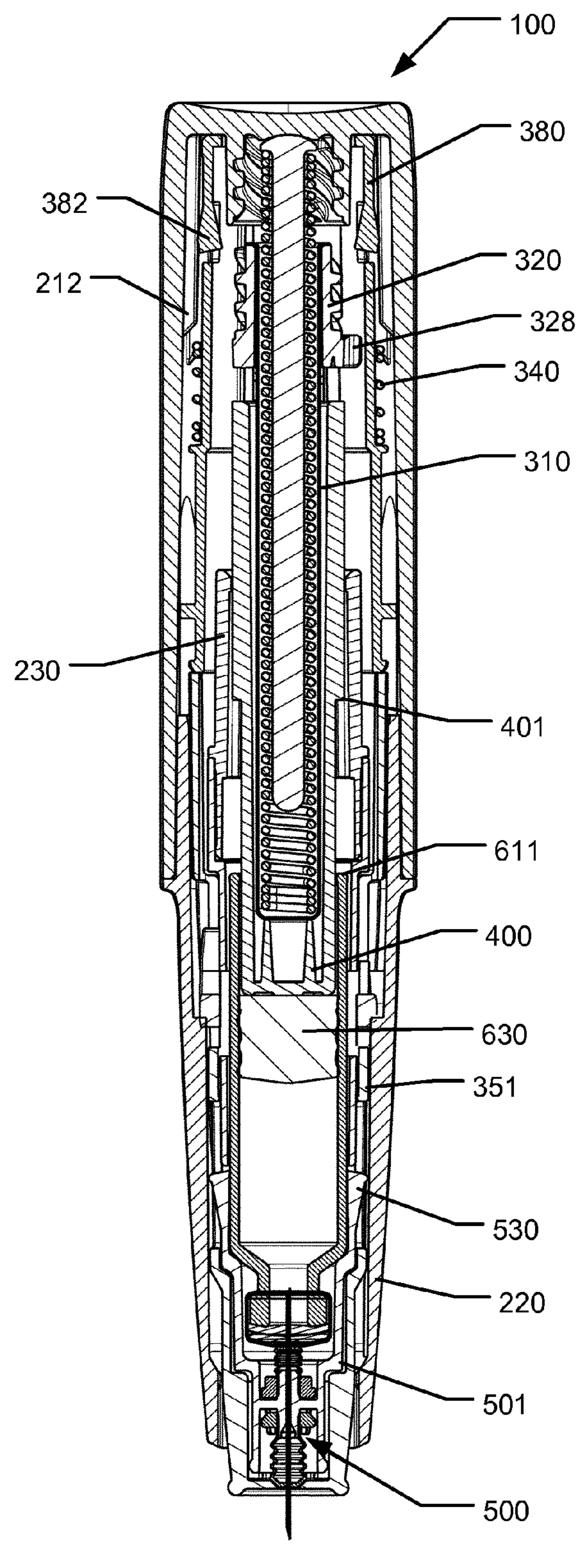
Figure 4A:
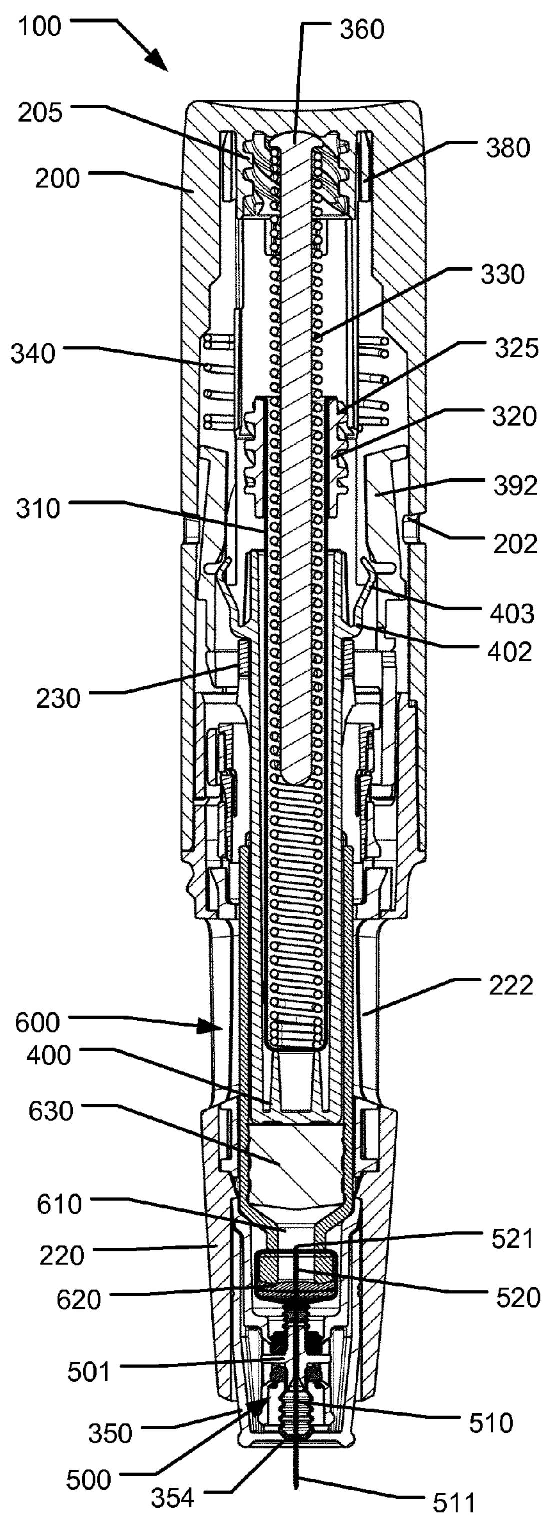
Figure 4B:
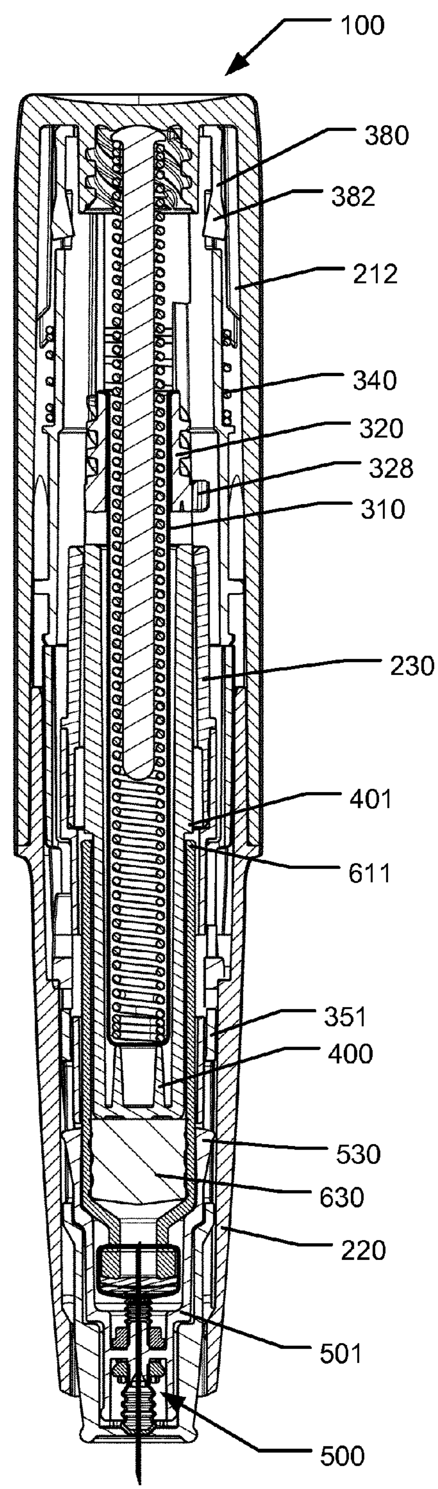
Figure 5A:
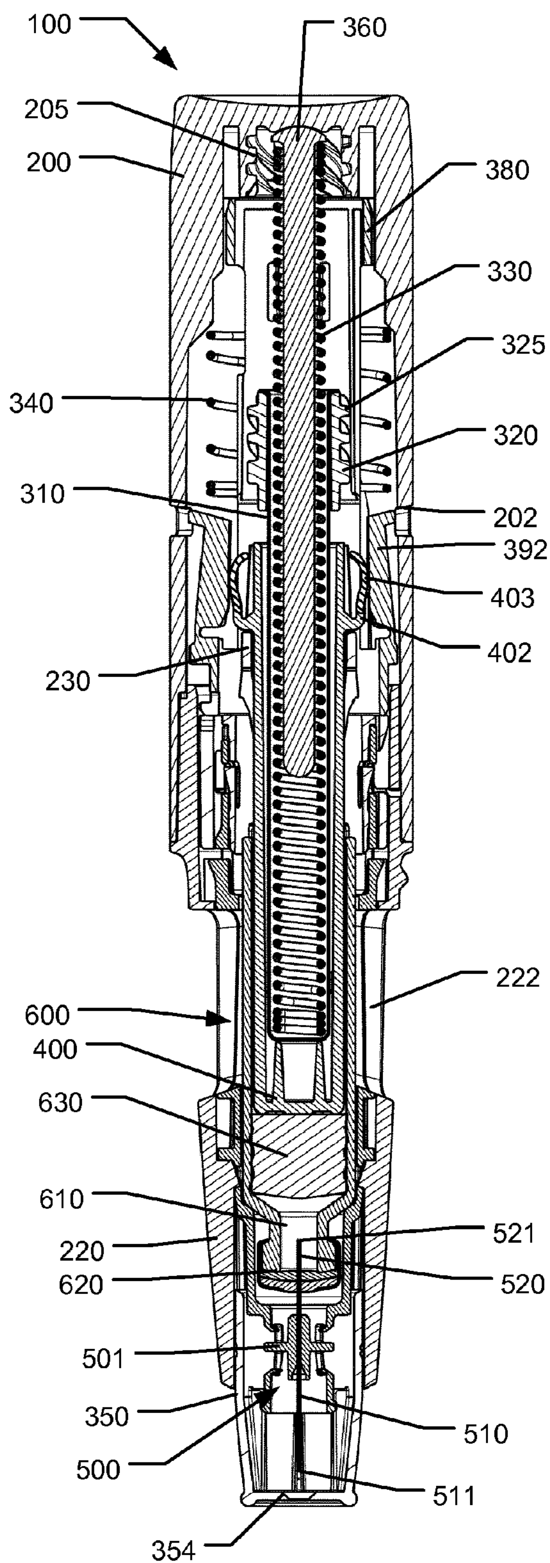
Figure 5B:
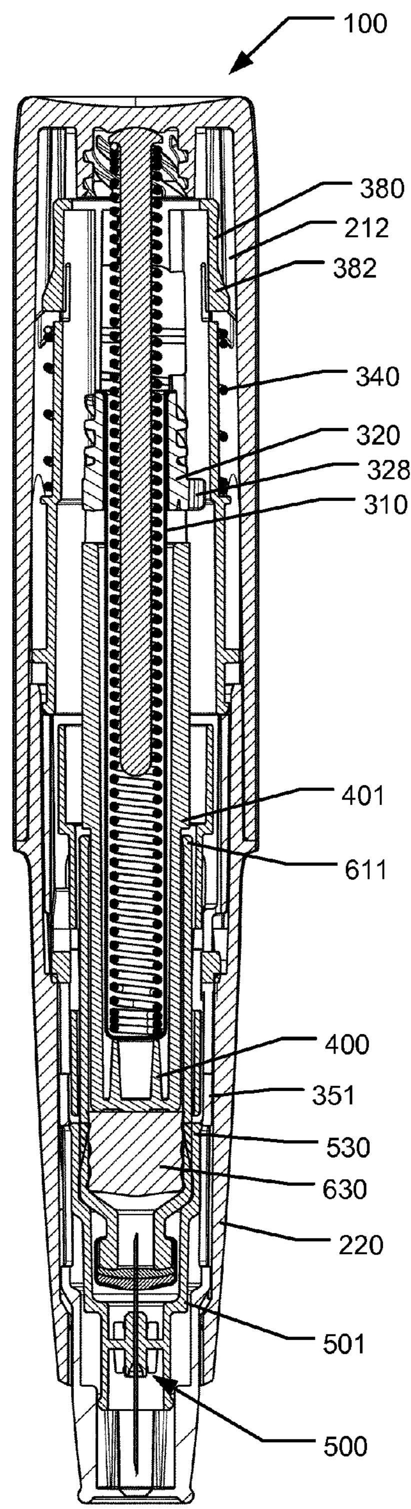
Figure 5C:
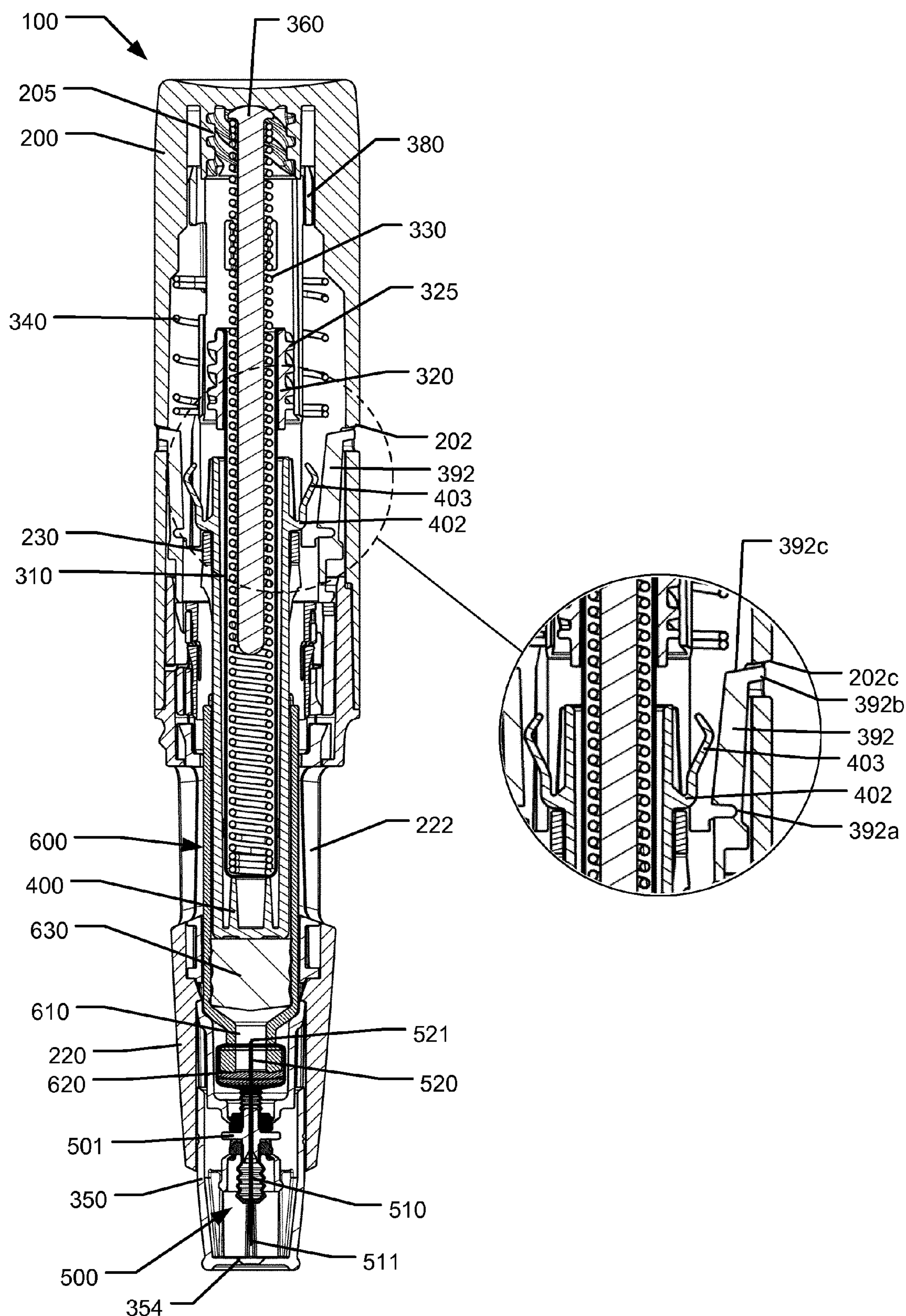
Figure 6:
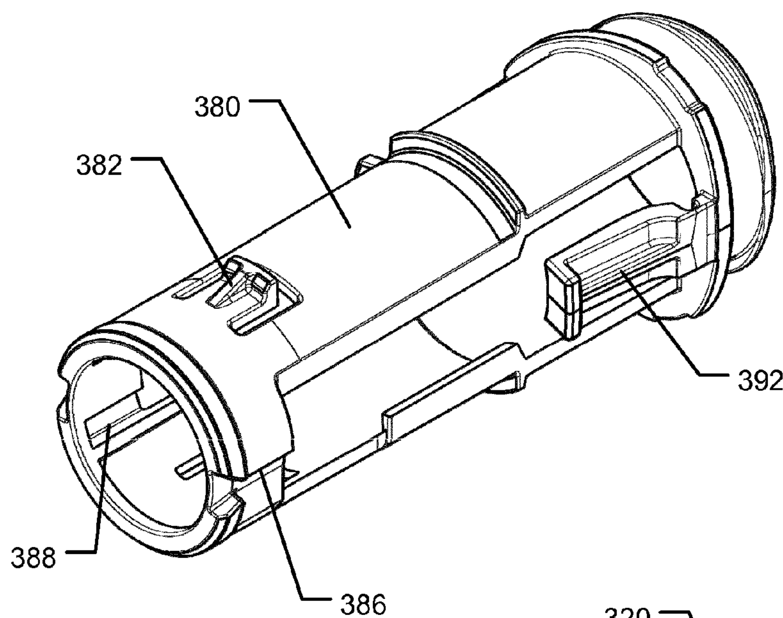
Figure 7:
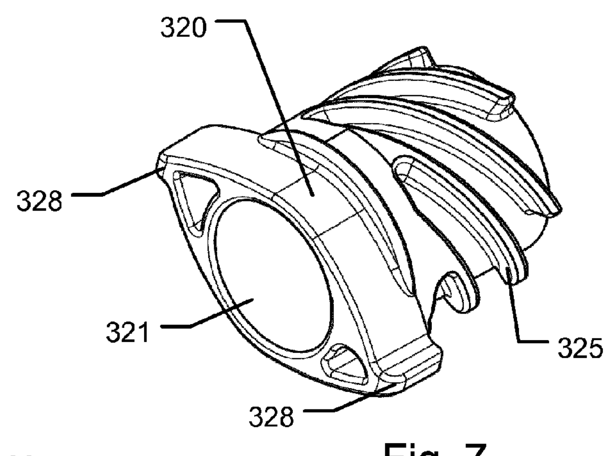
Figure 8:
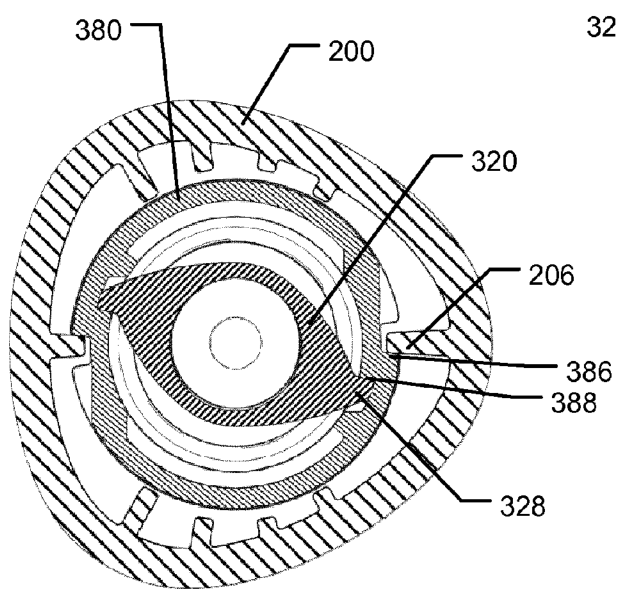
Figure 9A:
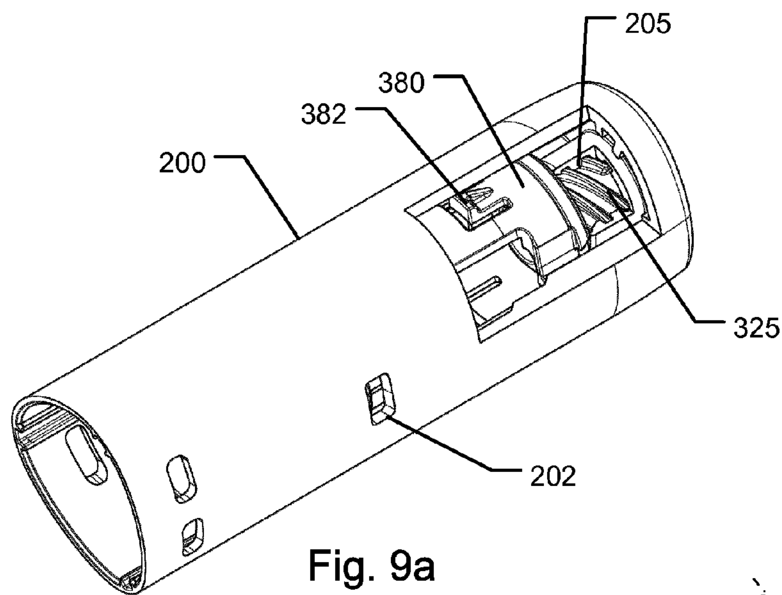
Figure 9B:
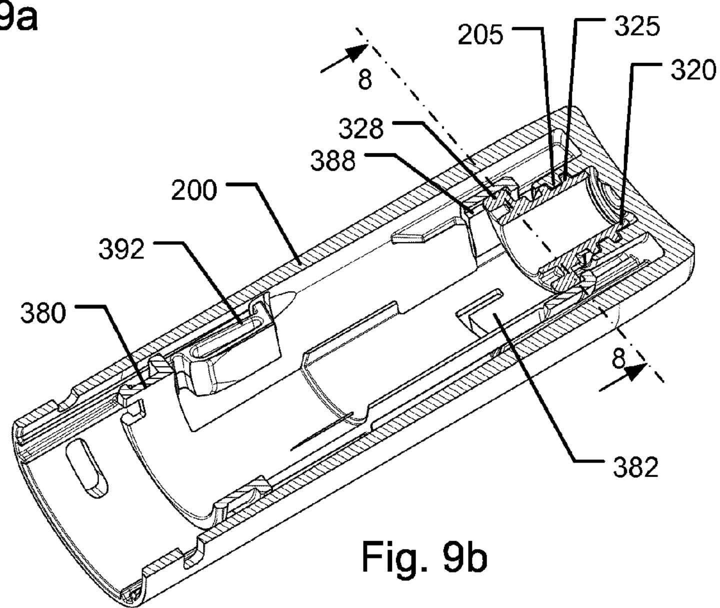
Figure 9C:
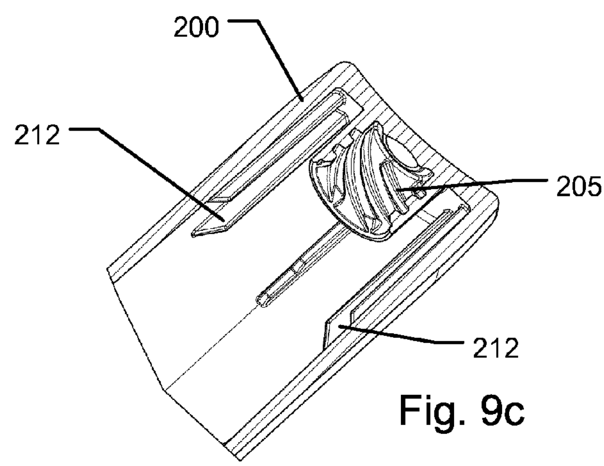

The invention will now be described in further detail with reference to the drawings in which:

FIGS. 1*a*, 1*b* and 1*c* show sectional front and side views of an exemplary embodiment of an injection device 100 according to the invention, the injection device being in an initial shielded state, FIGS. 2*a*, 2*b* and 2*c* show sectional front and side views of the device 100 illustrating a state where a front needle fully protrudes from a needle shield, FIGS. 3*a*, 3*b* and 3*c* show sectional front and side views of the device 100 illustrating a state where the cartridge has been connected to the needle for fluid delivery and wherein expelling has been initiated, FIGS. 4*a* and 4*b* show sectional front and side views of the device 100 illustrating a state where a predetermined dose of medicament from the cartridge has been expelled, FIGS. 5*a*, 5*b* and 5*c* show sectional front and side views of the device 100 illustrating a state where the needle shield has returned to the shielded state, FIG. 6 is a detailed perspective view of a trigger element of the device 100, FIG. 7 is a detailed perspective sectional view of a release nut of the device 100, FIG. 8 shows a cross sectional view of a release nut assembly of the injection device 100, FIG. 9*a* is a partly cut perspective view of a top housing section of the injection device 100, FIG. 9*b* is a cross sectional perspective view of the release nut assembly of the injection device 100, FIG. 9*c* is a partly cut cross sectional perspective view of the proximal part of the housing section 200, FIGS. 10*a*-10*d* show schematical views of a needle shield lock according to a first alternative embodiment in four different operating states, and FIGS. 11*a*-11*d* show schematical views of a needle shield lock according to a second alternative embodiment in four different operating states.

The following is a description of an exemplary embodiment of a medical injection device 100 for administering a pre-determined amount of a liquid medicament. The device 100 is an autoinjector configured for expelling a dose of a drug in a single administration whereafter the device 100 is ready for disposal. FIGS. 1*a* through 5*c* show various states of the injection device 100 during operation thereof with different views offering a detailed assessment of the operating principle.

It is to be noted that the group of FIGS. 1*c*, 2*c*, 3*c*, 4*a*, 4*b* and 5*c* depicts a few more components than shown in the remaining illustrations spanning the series of FIGS. 1*a*-5*c*. Said components however do not add to the understanding of the primary features of this disclosure. Furthermore, having regard to elements that during operation will deform into a deflected state, the first mentioned group of figures illustrates the true operational state of the deflected elements more correctly.

Injection device 100 includes an elongated housing that extends along a central longitudinal axis. Exemplary cross sectional shapes of the housing may include a circular housing, a polygonal housing or, as shown, exhibiting a more complex cross sectional shape (cf. FIG. 8). The housing forms a base that includes a lower housing section 220 arranged at a distal end of the device and a top housing section 200 arranged at a proximal end of the device. The lower housing section 220 and the top housing section 200 are joined to each other to form an enclosure to accommodate a medicament cartridge 600. In the shown embodiment, the base further includes a support member 230 which is mounted axially fixed relative to the top and lower housing sections 200/220.

Injection device 100 may further include a removable protective cap (not shown) that attaches to a distal end of the device 100 to protect a needle end of the device 100. The lower housing section 220 includes two opposing windows 222. When the cap has been removed from the device 100, the windows 222 allow visual inspection of the medicament contained within the device 100. In addition, windows 222 allow a user of the device to determine whether or not the device 100 has been used for an injection by inspecting the presence or the location of a piston of a medicament cartridge 600, or alternatively a plunger device, arranged within the housing. In the shown embodiment top housing section 200 is for manufacturing reasons formed as an element separate from but permanently fixed to lower housing section 220 but may in alternative embodiments be formed integral with lower housing section 220.

FIGS. 1*a*, 1*b* and 1*c* show front and side sectional views of the device 100 after the protective cap has been removed but in a condition prior to the administration operation. Shown protruding from the distal end of the lower housing section 220 is a needle shield 350 which is arranged coaxially and slidable relative to lower housing section 220. Needle shield 350 is slidable relative to the housing between a distal extended position where a front end of a needle assembly 500 arranged internally in lower housing section 220 is in a shielded state and a second proximal collapsed position where a front needle end of the needle assembly 500 protrudes through an aperture 354 arranged in the central part of a distal wall surface of the needle shield 350.

The injection device 100 is configured for being triggered to inject a dose when the needle shield 350 is moved from the distal extended position towards the collapsed position. The protective cap, when attached to the lower housing section 220, prevents the needle shield 350 from being manipulated and thereby prevents premature triggering of the injection device 100.

Lower housing section 220 accommodates a medicament filled cartridge 600 having an outlet 610 covered by a cartridge septum 620 adapted to be pierced by a needle for establishing fluid communication with the cartridge interior and having a slidably arranged piston 630. Piston 630 is driveable towards the outlet 610 when a needle pierces the cartridge septum 620 in order to dispense medicament from the cartridge 600. The dispensing is controlled by an expelling assembly. Cartridge 600 is arranged movable with respect to the lower housing section 220 from a proximal storage position to a distal active position.

Distally in the lower housing section 220 is a needle unit in the form of a needle assembly 500 arranged in an initially separated configuration with respect to cartridge 600. In the shown embodiment, needle assembly 500 includes a needle cannula having a front needle 510 and a rear needle 520 respectively protruding in the distal and proximal directions from a needle hub 501. Both front needle 510 and rear needle 520 include pointed tips 511 and 521 for respectively piercing the skin of a user and the cartridge septum 620.

As shown in FIG. 1*c*, the needle assembly 500 furthermore may include a front cover 512 and a rear cover 522 forming sterility sheaths for the front needle 510 and rear needle 520 respectively. Each of the front and the rear covers may be formed as a rubber sheath which is penetrable by the pointed tip portions of the needle 511/521 when the cover 512/522 is forced towards the needle hub 501. Prior to use of the device 100, each of the two covers 512/522 assumes the extended position in which the cover seals of the respective one of the front 510 and rear needle 520. The front and rear covers may be attached to the hub 501 either by gluing, welding, interference fit, a separate mounting element, or by corresponding means.

The needle cannula may be attached to the hub 501 by gluing, interference fit or similar joining process. In the embodiment shown, the hub 501 is an element separate from the housing but may in alternative embodiments be formed as a part of the housing 200/220. Hub 501 is formed as a generally tubular structure which extends proximally along the cartridge and even further to a position proximal to the cartridge. In this way the hub 501 supports the cartridge 600 along an exterior cylindrical wall of the cartridge. As such, the hub 501 is designed to perform as a cartridge holder relative to which the cartridge 600 is allowed to axially slide between the proximal storage position and into the distal active position.

In the shown embodiment, the needle hub 501 and hence the needle cannula is axially mounted relative to the housing of the device 100 so that the needle cannula follows axial movements of the housing when the housing is moved relative to the needle shield 350.

In the shown embodiment, the needle shield 350 is formed as a generally tubular member having a distal face arranged to initially cover the front needle 510 and the front cover 512. The needle shield 350 is mounted slidable relative to the lower housing section 220 allowing limited axial movement by a predefined axial distance.

The needle shield 350 cooperates with a trigger element 380 which is located proximally to the needle shield 350. Trigger element 380 is also formed as a generally tubular element and extends axially in the proximally direction from the needle shield to a location close to the proximal end of top housing section 200. In the assembled state of the device 100, the needle shield 350 and the trigger element 380 perform as a single entity, i.e. the movement of trigger element 380 follows axial movement of the needle shield 350. Hence the trigger element 380 is movable from a distal end position corresponding to the extended position of the needle shield 350 to a proximal end position corresponding to the collapsed position of the needle shield 350. In the shown embodiment, each of the needle shield 350 and the trigger element 380 are mounted in a way that prevents rotational movement relative to the housing 200/220. In other embodiments, the trigger element 380 and the needle shield 350 may be formed as a unitary component.

A needle shield spring 340 is arranged between the housing section 200 and the trigger element 380. The trigger element 380 is urged in the distal direction by means of the needle shield spring 340 so that when no external applied force is exerted on the needle shield, the needle shield assumes its distal extended position which is shown in FIGS. 1*a*, 1*b* and 1*c*. In this position a stop geometry on trigger element 380 and/or needle shield 350 prevents the two components from moving further in the distal direction. When an externally applied force is exerted on the needle shield 350 for moving the needle shield in the proximal direction relative to the housing, such as when device 100 is pressed with the needle shield against an injection site, the externally applied force acts counter to the force provided by the needle shield spring 340 resulting in the needle shield 350 and the trigger element 380 being forced to move in the proximal direction. When the needle shield 350 assumes the proximal collapsed position a proximal end surface of the trigger element 380 prevents the trigger element and the needle shield 350 from moving further proximally relative to the housing (cf. FIGS. 2*a*-2*c*).

As the device 100 is removed from the injection site, the needle shield 350 will move distally due to the force from the needle shield spring 340. After an injection has been performed, as the needle shield 350 reaches its distal position again, as shown in FIG. 5*c*, it will be locked in this position to render the needle shield inoperable (to be further explained below). While referring to "its distal position" it is to be noted that the shown device 100 is so designed that the said distal position where the needle shield is made inoperable corresponds to the initial distal position the needle shield assumes prior to triggering. However, in other embodiments, the final distal position where the needle shield is made inoperable may be located slightly different than the initial distal position prior to triggering, e.g. positioned at a slightly different axial position relative to the housing.

The needle assembly 500 is arranged at the distal end of the lower housing section 220, such that the needle shield 350 completely covers the needle assembly when the needle shield is in its extended position. When the needle shield 350 is in its proximal collapsed position, the front needle 510 protrudes through the aperture 354 of needle shield 350.

As indicated in FIG. 1*b*, the cartridge 600 is maintained in its proximal storage position by means of two resilient arms 530 that extend radially inwards from the needle hub 501. In the initial state shown in FIG. 1*b*, the resilient arms 530 assume a position where they support and retain a neck portion of the cartridge 600 to prevent the cartridge from moving in the distal direction. The resilient arms 530 are adapted to flex radially outwards when sufficient force acting to move the cartridge 600 in the distal active position is exerted on cartridge 600. However, in the initial state where the needle shield 350 assumes its distal extended position, a blocking geometry 351 of the needle shield 350 encircles the resilient arms 530 to prevent them from flexing outwards and thus prevents the cartridge 600 from being moved distally. As will be described later, the blocking geometry 351 is configured to move axially when the needle shield 350 is moved into its proximal collapsed position making room for the resilient arms 530 to be flexed radially outwards.

The expelling assembly of injection device 100 is based on a plunger device that is driven in the distal direction along the central longitudinal axis of the device for advancing the piston 630 to thereby expel a dose from the cartridge 600. The plunger device in the shown embodiment includes a drive ram 310 and a spacer member 400. In other embodiments, the plunger device may form a unitary element. In device 100 an actuator 330 is arranged in the proximal part of the device providing a stored energy source for exerting a distally directed force on drive ram 310. Spacer member 400 is a generally tubular member that is positioned between drive ram 310 and the piston 630 of the cartridge 600. Spacer member 400 acts as an intermediary member for transferring a force exerted by the drive ram 310 on the piston 630 for forwarding the piston in the distal direction. The spacer member 400 is mounted axially displaceable but is prevented from rotating relative to the housing 200/220.

The actuator is provided in the form of actuating spring 330 that in the shown embodiment is provided as a pre-stressed helical compression spring. The actuating spring 330 is energized by straining the compression spring during manufacture of the device. The drive ram 310 is furthermore hollow to allow the actuating spring 330 to be positioned within the drive ram 310. A guiding element 360 arranged internally in actuation spring 330 assists in guiding the actuation spring 330 to prevent it from bending sideways. Guiding element 360 provides at its proximal end a seat portion arranged to act as a seat for supporting the proximal end of actuation spring 330.

The spacer member 400 is formed with stop surfaces 401 positioned a predetermined distance from the distal end of spacer member 400 to cooperate with the rear end 611 of the cartridge 600 to thereby define a precise end of stroke position for the piston 630 inside cartridge 600. As the piston 630, during filling of the cartridge 600, can be accurately positioned with respect to the rear end 611 of the cartridge 600, the exact volume of an expelled dose can be accurately controlled by utilizing the stop surfaces 401 hitting the rear end 611 of cartridge 600 at completion of the expelling operation.

In the embodiment shown, spacer member 400 and a cooperating support member 230 fixedly attached to or associated with the housing 200/220 may further include one or more pairs of click generating elements such as protrusions adapted to cooperate with click arms to generate click sounds during and/or at the completion of the injection.

As mentioned, in the shown embodiment, the actuator in the form of a pre-stressed actuation spring 330 urges the drive ram 310 in the distal direction. In the unactivated state of the injection device 100, a release nut 320 associated with drive ram 310 cooperates with the top housing section 200 and the trigger element 380 to retain the drive ram 310 in an initial axial position against the force of the actuation spring 330. Upon activation of the expelling assembly, i.e. by operating the trigger element, the release 320 nut is released allowing the drive ram to thrust forward for providing a distally directed force on the piston 630.

Alternatively to using a pre-stressed spring which is compressed during manufacture of the device, other embodiments of autoinjectors may include a mechanism for compressing the spring as an initial procedure when putting the device into use. Also, the actuator may in other embodiments be formed as a torsion spring which is pre-stressed to exert a torsion force for driving forward a rotational drive of the expelling assembly. Alternatively, the actuator may be in the form of a compressed medium such as a gas. Still alternatively, the actuator may include a gas generator such as an electro-chemical cell.

The drive ram 310 is provided as a deep-drawn metal tube extending along the central longitudinal axis and defining a closed distal end and an open end portion having a collar extending radially outwards at its proximal end. The release nut 320 is arranged at the proximal end of the drive ram 310 to encircle the drive ram 310. Release nut 320 has an axial bore 321 defining a circumferential collar that rests against the collar of the drive ram 310 to prevent the drive ram 310 from moving distally relative to release nut 320. In the shown embodiment, the release nut 320 is freely rotatable relative to drive ram 310. However, in other embodiments, the release nut 320 may be fixedly attached with respect to drive ram 310 or formed integrally therewith. In the shown embodiment the release nut 320 is rotatable around a rotational axis which is coaxial with the central longitudinal axis mentioned above.

Shown in greater detail on FIGS. 9*a*-9*c* release nut 320 defines a thread 325 that engages a thread 205 associated with the housing section 200 when the device 100 is in the initial state prior to triggering. A releasable trigger lock acts to prevent relative rotation between the release nut 320 and the housing section 200, thereby maintaining the drive ram 310 in the initial axial position.

In the shown embodiment, the trigger lock is provided by the trigger element 380 preventing relative rotation between the release nut 320 and the housing section 200. As shown in FIGS. 6 and 8 axial tracks 386 of trigger element 380 are configured to be engaged by respective axial ribs 206 of top housing section 200 preventing the trigger element 380 from rotation relative to the housing 200/220 but enabling axial displacement. In the shown embodiment, two radially outwards extending protrusions 328 of release nut 320 are adapted to engage corresponding axial tracks 388 extending radially inwards on an inner surface of trigger element 380 (see FIGS. 5, 6 and 7). The axial tracks 388 each has a limited axial length defining circumferential neighbouring areas that are open at a location at the distal end of axial tracks 386. When sufficient axial displacement of release nut 320 relative to the trigger element 380 occurs, rotation of release nut 320 is enabled. But in the initial state prior to triggering, as long as the trigger element 380 is situated distally relative to a pre-defined triggering position, the release nut 320 is prevented from rotating. The triggering position of the trigger element 380 is located at a point in close proximity but distally to the proximal end position of the trigger element 380.

As long as the release nut 320 is prevented from rotating relative to the housing the threaded engagement between the thread 325 of the release nut 320 and the thread 205 of the housing prevents the release nut 320 from being moved axially. Hence, prior to activation of the expelling assembly, the drive ram 310 is also prevented from being moved in the distal direction as long as the trigger element 380 is located distal to the triggering position. In the shown embodiment, thread 325 and thread 205 are dimensioned to provide large surface areas to take up the force from actuator 330, enabling the use of plastic materials for the thread components.

The lead of the threaded connection 325/205, the length of the threads and the dimensions of the engagement between the protrusions 328 and the axial tracks 388 are so configured that, upon displacement of the trigger element 380 towards the triggering position, once the release nut 320 has been released for rotation and thus rotated slightly, the protrusions 328 cannot reengage the axial tracks 388. Hence, once the expelling assembly has been activated by exerting a force on the needle shield 350 for triggering the device, in case of a potential release in the force exerted on the needle shield, the distal movement of the drive ram 310 cannot be interrupted, i.e. the drive ram 310 will continue its distal movement until the intended end of dose position defined by the elements 401/611.

FIG. 9*a* shows a partly cut perspective view of the top housing section 200 wherein the trigger element are and the release nut 320 are visible. The release nut 320, the trigger element 380 and the top housing section 200 together forms a release nut assembly. For clarity, the depicted view only shows selected components of the injection device 100 in the initial state prior to triggering but wherein additional components such as the actuating spring 330 and the drive ram 310 are omitted. The engagement between the thread 325 of the release nut 320 and the thread 205 of the housing section 200 is visible. FIG. 9*b* shows the release nut assembly in a sectional perspective view.

Referring back to FIG. 1*c*, 5*c* and FIG. 6, the trigger element 380 includes a plurality of deflectable lock elements 392 formed as a pair of resilient or deflectable arms that partly constitutes a needle shield lock which renders the needle shield 350 permanently arrested when the needle shield, subsequent to finalisation of an injection, is returned to the extended position. As shown in FIG. 5*c*, the resiliency of each of the deflectable lock elements 392 is confined to a film hinge section 392*a* that connects the respective deflectable arm with the remaining of the trigger element 380. Each of the deflectable lock element 392 comprises a rigid beam section extending from its distal end at the hinge section 392*a* towards a proximal end 392*b*.

Each of the deflectable arms 392 is configured to be flexed or deflected radially outwards away from a passive unbiased configuration and into a biased active configuration where the needle shield lock is provided. The passive unbiased configuration is best viewed in FIG. 1*a*. Each of the deflectable arms 392, at the proximal end 392*b*, forms an outer protrusion that is configured to enter into a corresponding recess 202 formed in top housing section 200 when the needle shield 350 is to be arrested. The biased active configuration is best viewed in FIG. 5*c*.

The said needle shield lock further incorporates a lock activator associated with the plunger device, such as an activation geometry arranged on the plunger. In this embodiment, the lock activator is defined by a pair of activation arms 402 formed by and extending radially outwards from the spacer member 400. Each of the activation arms 402 includes a resilient section 403 that provides resiliency in the radial direction. When the axial position of the activation arms 402 corresponds to the axial position of the deflectable arms 392, each of the activation arms 402 cooperates and exerts a radially outwards directed force on a respective deflectable arm 392 to urge the proximal end 392*b* of deflectable arm 392 radially outwards. However, the radially outwards force exerted by the activation arm 402 only moves the deflectable arm 392 outwards and into its corresponding recess 202 after the drive ram 310 has reached its end of dose position and when the protrusion of each of the deflectable arms 392 is aligned axially with its corresponding recess 202. When the protrusion of each of the deflectable arms 392 does not align axially with its corresponding recess 202, the deflectable arm 392 is prevented from moving radially outwards. By comparing FIG. 2*a* and FIG. 3*a* it becomes clear that the resiliency of resilient section 403 enables each of the activation arms 402 to pass its respective deflectable arm 392 during forward movement of the spacer member 400. During this sequence, the deflectable arms 392 are not deflected radially outwards due to their proximal ends 392 being held in their passive unbiased configuration by the top housing section 200.

The needle shield 350 or the trigger element 380 may further comprise one or more contact surfaces each being resiliently slideable over a respective cooperating ramp surface formed in the housing. Referring to FIGS. 1*c*, 6 and 9*c*, in the shown embodiment, the contact surfaces are provided by trigger element 380 as a pair of resilient snap arms 382 that are adapted to deform radially inwards relative to the shown unbiased position. Each snap arm 382 is configured to cooperate with a respective ramp section 212 formed along an internal wall surface in the proximal part of housing section 200. As best viewed in FIG. 2*c*, each ramp section 212 is formed as an axial extending rib that is provided with a chamfered distal front section allowing the snap arm 382 to be deformed by the chamfered section of ramp section 212, when the trigger element 380 is moved from the distal end position to the proximal end position. The chamfered section of ramp section 282 connects to a ramp segment that continues in the proximal direction with a constant height, i.e. the ramp has an inner ramp surface extending parallel or substantial parallel with the rotational axis.

When the needle shield 350 is moved from the distal extended position towards the proximal collapsed position, the snap arms 382 of the trigger element 380 and the corresponding ramp sections 212 provide resistance to movement of the trigger element 380 and thus also resistance to movement of the needle shield 350. Upon applying the autoinjector 100 at an injection site, a high axial reaction force is created initially when the snap arms 382 engage the chamfered sections of ramp sections 212. Thus a high force exerted on the needle shield 350 is required in order for the snap arms 382 to climb the ramp sections 212. As soon as the snap arms 382 have climbed the ramp sections 212, resulting in the snap arms 382 have been deformed radially inwards, the snap arms 382 travel and slide along the constant height ramp segments as the needle shield 350 is pushed further proximally relative to housing 200/220. This action requires considerable less force to be applied on the needle shield 350 than the initial high force. Hence the needle shield displacement will occur in two stages, i.e. a first high force stage and a second low force stage.

It will be appreciated, that the force needed for proximally displacing the needle shield will be largely independent from the force provided by the actuator 330, but will rather be decided by the force of the needle spring 340 and the force profile for the interaction between the snap arms 382 and the ramp sections 212. During displacement of the needle shield 350 relative to the housing 200/220, the frictional force acting against movement emanating from the force exerted by actuator 330 will be constant.

As will be discussed further below, the above mentioned pre-defined triggering position of trigger element 380, and the corresponding position of needle shield 350, will be situated at the final part of the proximal movement of the needle shield where the snap arms 382 travel along the constant height ramp segments of ramp sections 212.

The high initial needle shield displacement over a short distance assures that the needle shield is fully displaced and the autoinjector is effectively triggered due to the inertia of the human motion. In accordance herewith, the triggering point may be positioned at a location where the snap arms 382 engage the ramp sections 212 at the constant height ramp segments, preferably within the most proximal half of the path of interaction between the snap arms 382 and the constant height ramp segments of ramp sections 212.

The autoinjector may be so configured that the front cover 512 is only penetrated by the front needle 510 once the high initial force for bending the snap arms 382 radially inwards has been overcome. Hence, the risk that a non-triggered but broached device may occur will be minimal.

In the following, while mainly referring to FIGS. 1*a* through 5*c*, operation of the injection device 100 will be described.

As a first step in operating device 100, the previously mentioned protective cap is removed from the device. As mentioned above, FIGS. 1*a*-1*c* show the device in a state corresponding to its initial storage condition but with the protective cap being removed from the housing 200/220. The needle shield 350 is in its extended position whereby the front needle 510 is in a shielded state. Also the rear needle 520 is in a shielded state as the cartridge 600 assumes its initial position situated apart from the needle assembly 500.

In accordance with the above description, the housing 200/220 acts as an activator relative to the needle shield 350, in that, as the housing is gripped by the hand of the user and the distal end of device 100 is pressed against an injection site, the needle shield 350 will remain arrested relative to the skin and the housing moves distally relative to the needle shield 350 for activating the expelling assembly of the device 100.

As the device 100 is activated (cf. FIGS. 2*a*-2*c*) the needle shield 350 is moved in a proximal direction relative to lower housing section 220 with the distal end surface of the needle shield 350 moving towards the needle assembly 500. The movement brings the front needle 510 through the small aperture 354 in the needle shield 350. As the needle cannula moves relative to the aperture 354 the above mentioned front cover 512 (see FIG. 2*c*) is preferably held back by the geometry around the aperture 354, thereby allowing the front needle 510 to penetrate the front cover 512 while front cover is being compressed between the needle shield 350 and the needle hub 501. Alternatively the front cover could move through the aperture 354 as well. In such case the front cover would be pressed against the patient's skin, thereby being compressed between the device 100 and the injection site. The compression of the front cover can be either in a concertina-like way or be bent sideways, e.g. radially outwards. The front cover may have a specific geometry to ensure that the front cover is always compressed between needle shield 350 and needle hub 501. The aperture 354 in the needle shield 350 could also have a specific geometry for ensuring correct compression of the front cover.

In the state shown in FIGS. 1*a*-1*c* the trigger element 380 is in its distal position due to the pressure exerted by the needle shield spring 340. Cf. to FIG. 9*b*, the releasable trigger lock that rotationally locks the release nut 320 relative to the housing 200/220 is enabled and the drive ram 310 is therefore in its initial position. The cartridge 600 is positioned in its proximal storage position. The snap arms 382 have climbed the ramp sections 212, resulting in the snap arms 382 having been deformed radially inwards by the ramp sections 212 (see FIG. 2*c*).

As the needle shield 350 reaches a predetermined position, i.e. the proximal collapsed position, the needle shield 350 will reach a stop limit, see FIGS. 2*a*, 2*b* and 2*c*. In this state the front needle 510 is inserted in the patient's skin and the front cover 512 is compressed (see FIG. 2*c*). In accordance with the movement of the needle shield 350, the trigger element 380 has been moved into its proximal position, i.e. past the triggering position.

As the trigger element 380 has been moved into its proximal position, the axial tracks 388 of trigger element 380 will become displaced so as to disengage from the engagement with the protrusions 328 of release nut 320. This situation is best viewed in FIG. 2a. Due to the actuating spring 330 is exerting a force in the distal direction on drive ram 310 and release nut 320 the non-self-locking threaded engagement 325/205 will induce the release nut 320 to rotate. In FIGS. 2a and 2b, the release nut 320 has been rotated slightly relative to top housing section 200 and, in accordance with the threaded engagement, the release nut 320 and the drive ram 310 have been moved slightly axial towards the distal direction. The initial spacing between the drive ram 310 and the spacer member 400 has been eliminated so that the force of the actuating spring is enabled to act on the piston 630 of cartridge 600 by means of the drive ram 310 and the spacer member 400.

The needle shield 350 and thus the blocking geometry 351 have been moved in the proximal position so that the resilient arms 530 are free to become deflected outwards. As shown in FIG. 3a-3c the force from the actuation spring 330 firstly displaces the drive ram 310, the spacer member 400 and the piston 630 a distance in the distal direction. During the first part of this stage the rear needle 520 is still separated from the septum 620 of the cartridge 600 and the cartridge is thus forced to move with the piston 630. The force of actuating spring 330 is sufficient to overcome the force needed for deflecting the resilient arms 530 outwards. Note however, that in FIGS. 3b and 4b, the resilient arms 530 are shown superposed relative to the wall sections of the cartridge 600. A more correct depiction of how the resilient arms 530 are actually deflected can be viewed in FIGS. 3c and 4b.

Initially, as the cartridge 600 moves distally, the distance between the stop surface 401 of the spacer element 400 and the rear end 611 of the cartridge 600 remains unchanged as the piston 630 generally does not move relative to the body of the cartridge 600. However, after the cartridge 600 has been moved fully in the distal direction, the piston 630 begins its movement inside cartridge 600, the said distance decreases. As noted above, the resiliency of the activation arms 402 enables the activation arms to deflect radially inwards and axially pass the deflectable arms 392. In some embodiments, the deflection of the activation arms 402 may act to reduce the impact between the cartridge 600 and the needle hub 501 as the cartridge enters the distal active position.

In the state shown in FIG. 3c cartridge 600 has been moved fully into its distal active position where it meets a stop feature formed in the needle hub 501. The rear needle 520 has penetrated the rear cover 522 and the rear cover has been compressed by the force exerted by the septum 620 of cartridge 600. Further, the rear needle 520 has penetrated the septum 620 of the cartridge. Hence, fluid communication between the needle cannula and the medicament contained in the cartridge 600 has been enabled. In this position the needle cannula is in contact with both the patient's skin and the medicament contained in the cartridge 600. After fluid communication between needle cannula and cartridge 600 is established the medicament is injected into the patient by means of the drive ram 310 being now forced relative to top housing section 200 and being urged distally by actuating spring 330. In the state shown in FIGS. 3a and 3b, the force exerted by the actuating spring 330 has acted on the drive ram 310 for expelling a first portion of the fluid from the cartridge 600.

The force from actuating spring 330 continues to act on the piston 630 advancing the piston to a predefined end of dose position determined by the end of dose feature. When the stop surface 401 of spacer element 400 reaches the rear end 611 of the cartridge 600 the movement of the drive ram 310 is stopped, thereby stopping the expelling of the medicament (cf. FIG. 4b).

FIGS. 5a-5b and 5c show states of the injection the device 100 after it has been retracted relative to the injection site. As the device is removed the needle shield 350 is moved forward relative to the lower housing section 220, the needle shield being urged by means of the needle shield spring 340, thereby releasing the compressive pressure on the front cover 512 (not shown in FIGS. 5a and 5b). In the shown embodiment, the front cover 512 remains in its collapsed position. In alternative embodiments the front cover will tend to return to its extended position covering the front needle 510.

As the device 100 is removed from the patient the front needle 510 is removed from the skin of the patient. In embodiments where said front cover 512 returns to its extended position, the front cover will prevent excess medicament that is expelled from the needle cannula from dripping out of the device. The rear cover remains in its collapsed position due to the pressure from the cartridge 600.

As discussed above the needle shield 350 includes a needle shield lock which renders the needle shield 350 locked against proximal movements once it has been returned from the proximal collapsed position to the distal extended position, i.e. where the front needle 510 is in its shielded state. However, this is designed to occur only if the spacer member 400 is situated in the end of dose position or in positions in close vicinity to the end of dose position.

FIG. 5a shows the injection device 100 just prior to locking of the needle shield 350 where the needle shield has moved to the distal extended position and where the axial position of the deflectable arms 392 align with the corresponding recesses 202 in top housing 200. In FIG. 5a the proximal end 392b of deflectable arms 392 have only initially begun to move radially outwards.

Referring particularly to FIG. 5c, in the final state of the autoinjector 100, the proximal end 392b of deflectable arms 392 have been pressed radially outwards into their biased active configuration by resilient parts 403 of the activation arms 402 of spacer member 400. As the axial position of the protrusions of the deflectable arms 392 have been aligned with the axial position of the corresponding recesses 202 in housing 200, the radially outwards movement of deflectable arms 392 are allowed and hence the deflectable arms 392 are moved into locking engagement directly with the housing section 200. The spacer member 400 will be prevented from moving in the distal direction, either by being still forced distally by actuating spring 330 or by other means. Hence, the activation arms 402 maintain an outwardly directed force on the deflectable arms 392 preventing the deflectable arms from being moved radially inwards. The hinge section 392a of the deflectable arms may be so designed that the activation arms 402 need only provide a small force on the deflectable arms 392 to maintain the deflectable arms in their active configuration. Hence, the risk of creep of the materials is not likely to occur on activation arms 402 or deflectable arms 392. In this respect it is also to be noted that in the initial storage condition of the injection device 100, both the activation arms 402 and the deflectable arms 392 assume their unbiased position thereby also minimizing the risk of creep.

During expelling of the intended dose, the spacer member 400 moves distally in a desired stroke during which the activation arms 402 move distally from a proximal start position to a distal end position. In the shown embodiment, the activation arms are configured to overlap axially and cooperate with the respective deflectable arm 392 only when the activation arms 402 assume a limited range of axial positions in vicinity of the distal end position. Hence, when the activation arms 402 are positioned proximally to said range of axial positions, the activation arms 402 will not be able to cooperate and exert a radially outwards directed force on the respective deflectable arm 392. Hence, the needle shield lock function will only be enabled at the end of the dose stroke and only subsequent to the user withdrawing the device 100 from the injection site.

During the expelling procedure and before the activation arms 402 assume an axial position in vicinity of the distal end position, should the user prematurely withdraw the injection device 100 from the injection site the needle shield spring 340 will push the trigger element 380 and thus the needle shield 350 into its distal extended position. However, as the needle shield 350 will not have entered into a locked state, a renewed penetration at a new injection site will be possible and the user will be able to inject and receive the remaining portion of the intended dose.

Close inspection of FIG. 5*c* reveals that a proximal facing surface 392*c* of each of the deflectable arms 392 and the corresponding distal facing surface of the recesses 202 are formed with inclined sections tending to move the deflectable arms 392 radially outwards towards their active configuration when increasing pressure is exerted in proximal direction on the needle shield 350. Hence, the locking of the needle shield in the distal extended position is effectively obtained should excessive forces be applied onto the needle shield 350 acting to move the needle shield in the proximal direction. Hence the needle shield locking function is safely maintained. Following a possible recapping of the autoinjector 100 the device is ready for disposal.

As an alternative to the needle shield lock described above in relation to device 100 shown in FIGS. 1*a* through 9*c*, FIGS. 10*a*-10*d* show a needle shield lock according to a first alternative embodiment. In one example, the needle shield lock according to the first alternative embodiment may be incorporated in a device similar to the device 100. FIGS. 10*a* to 10*d* schematically show four different stages of operation of components relevant for the needle shield lock according to the first alternative embodiment. For reasons of clarity components that are not necessary to the understanding of the needle shield lock mechanism have been omitted. Relative to the figures for the device 100, corresponding parts in FIGS. 10-10*d* share similar reference numbers followed by an apostrophe, i.e. top housing section 200 corresponds functionally to top housing section 200' etc. In the figures, the needle end, i.e. the distal end, is located at the right hand side.

Each of the FIGS. 10*a* through 10*d* show a top housing section 200', a trigger element 380' arranged to be operated for axial movement by a not shown needle shield. Also shown is a spacer member 400' associated with a plunger device adapted to move along a central axis. Spacer member 400' comprises a lock activator 402' which in the shown embodiment is provided as a widening of the spacer member 400' at a particular axial location. Top housing section 200' includes a retaining or locking geometry in the form of a recess 202'. The trigger element 380' includes a deflectable arm 392' which in FIG. 10*a* extends generally parallel to the central axis from a proximal end to a distal end. The distal end connects via a hinge relative to the remaining of the trigger element 380'. Hence, the proximal end of deflectable arm 392' is able to swivel radially outwards relative to the position shown in FIG. 10*a*. At a radially inwards facing surface of deflectable arm 392' a biasing means 393' in the form of a resilient arm is arranged, the biasing means being configured to cooperate with the lock activator 402'. The biasing means 393' provides resiliency in the radial direction. When the lock activator 402' is not axially overlapping the biasing means 393', i.e., when the spacer member 400' assumes a position other than the end of dose position, the biasing means 393' slides along the narrow part of spacer member 400', either in abutting contact there with or without contact.

Figure 10A:
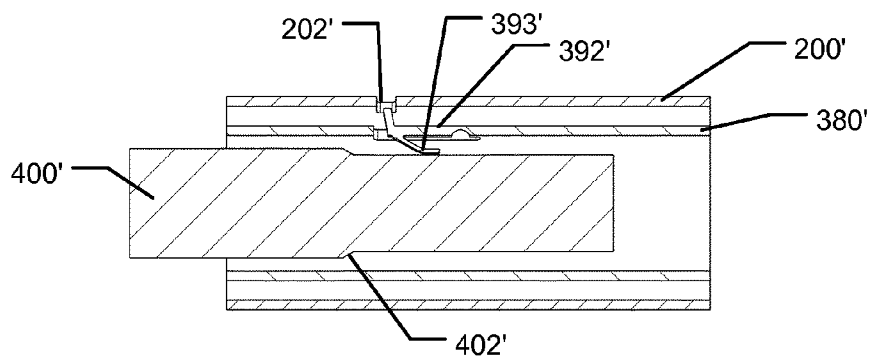

In FIG. 10*a* which illustrates the needle shield lock mechanism in a state corresponding to the state prior to use, i.e. prior to proximal movement of the needle shield, the trigger element 380' assumes a distal position. In the shown embodiment, the proximal end of the deflectable arm 392' is positioned at the same axial position as the recess 202' of the top housing section 200'. The spacer member 400' assumes an initial proximal position. The biasing means 393' may abut the spacer member 400' but does not cause the deflectable arm 392' to move outwards.

Figure 10B:
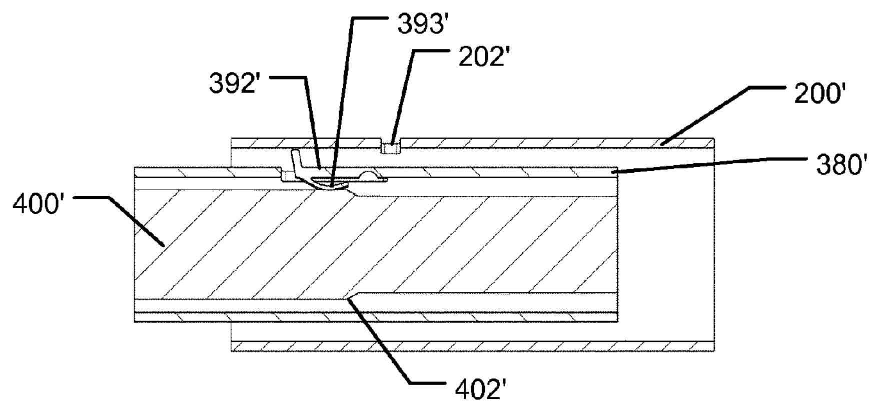

In FIG. 10*b* the needle shield has been moved proximally to trigger the device and the trigger element 380' assumes its proximal position. Hereby, the proximal end of the deflectable arm 392' has been moved axially away from the recess 202'. The biasing means 393' assumes a position where it axially overlaps the lock activator 402' and the lock activator provides an activation force on the biasing means 393'. As the deflectable arm 392' is prevented from moving radially outwards, the biasing means 393' is compressed in the radial dimension.

Figure 10C:
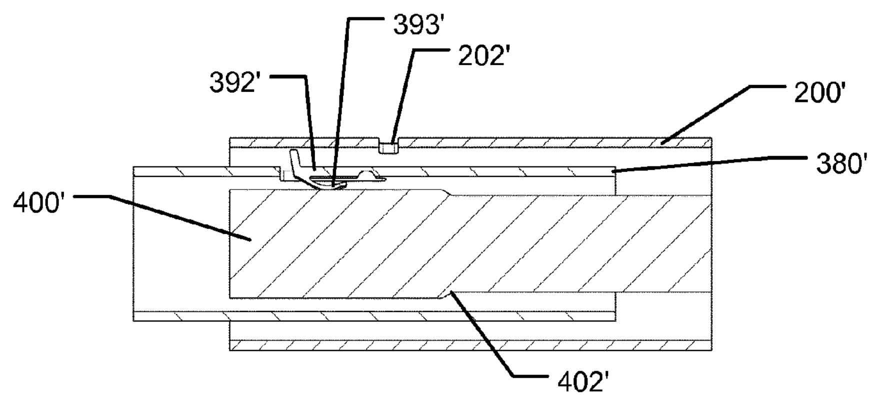
Figure 10D:
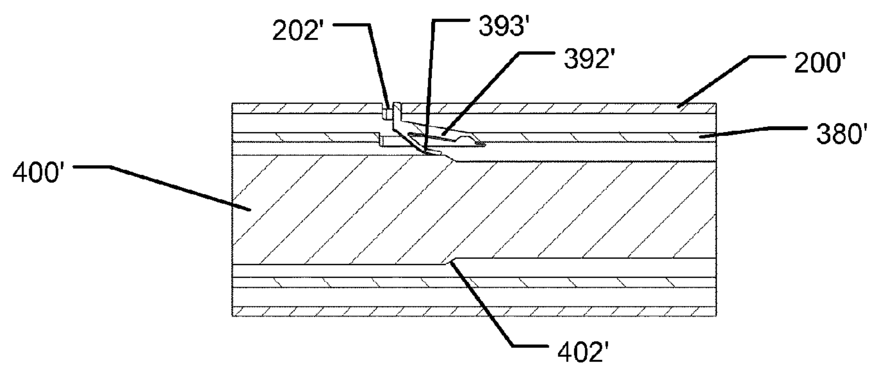

Proximal movement of the trigger element 380' in the state shown in FIG. 10*b* has caused the triggering of the device for initiating the expelling operation. This releases the spacer member 400' to move distally towards the end of dose position which is shown in FIG. 10*c*. Accordingly, the lock activator 402' has moved distally to enter into a distal position. Apart from this no other changes of the needle shield lock elements have been caused.

Subsequently to the spacer member 400' has reached the end of dose position as shown in FIG. 10*c*, the device may be withdrawn from the injection site. This moves the trigger element 380' towards its distal position again, see FIG. 10*d*. The proximal end of the deflectable arm 392' has been returned to its initial axial position aligned at an axial position with respect to the recess 202' of the top housing section 200'. Due to the resiliency of the biasing means 303', the activation force of the lock activator 402' that acts on the biasing means 393' causes the deflectable arm 392' to be forced radially outwards and into locking engagement with the recess 202' of the top housing section 200'. In this state, the needle shield will be permanently prevented from moving in the proximal direction and thus become finally locked.

In the first alternative embodiment shown in FIGS. 10*a*-10*d* the biasing means is strained in the state shown in FIG. 10*b*. In other alternative embodiments, the lock activator 402' could be arranged at a different axial location on the spacer member 400' so that the biasing means 393' is not caused to be strained when the trigger element 380' is positioned in the proximal position but only during dose expelling and when the spacer member 400' assumes its end of dose position.

A still further second alternative embodiment for a needle shield lock is shown in FIGS. 11*a*-11*d*. Relative to the figures for the device 100, corresponding parts in FIGS. 11*a*-11*d* share similar reference numbers followed by two apostrophes, i.e. top housing section 200 corresponds functionally to top housing section 200" etc. In the figures, the needle end, i.e. the distal end, is again located at the right hand side.

Figure 11A:
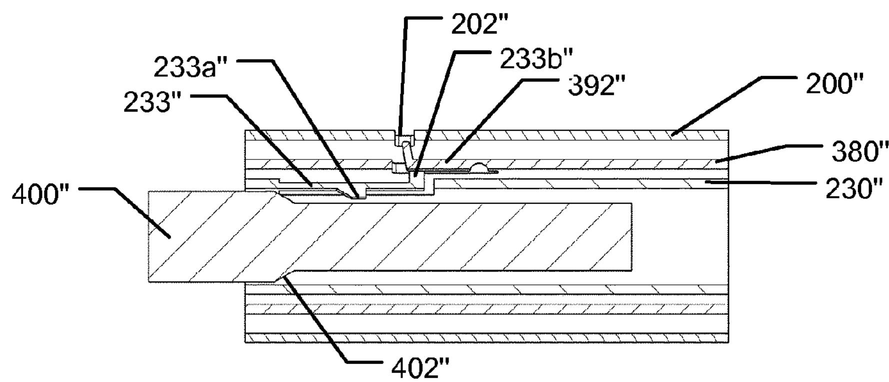

Compared with the first alternative embodiment shown in FIGS. 10*a*-10*d*, the embodiment shown in FIGS. 11*a*-11*d* differs in that the biasing means is provided as a resilient arm 233" that is arranged at an axially fixed location relative to the housing. FIG. 11*a* shows a support member 230" in form of a sleeve shaped member which is mounted axially fixed relative to the top housing section 200". The support member 230" is arranged radially between the trigger element 380" and the spacer member 400". In the shown example, the resilient arm 233" extends from a proximal end where it connects to the support member 230" and in the distal direction towards a free distal end. A radially inwards extending protrusion 233*a*" is configured for cooperating with the lock activator 402" when the lock activator 402" assumes a range of distal positions corresponding to the end of dose position for the spacer member 400". A radially outwards extending protrusion 233*b*" is configured for cooperating with the deflectable arm 392" but only when the trigger element 380" is located in proximity of its distal position.

In FIG. 11*a* which illustrates the needle shield lock mechanism in a state corresponding to the state prior to use, i.e. prior to proximal movement of the needle shield, the trigger element 380" assumes a distal position. In the shown embodiment, the proximal end of the deflectable arm 392" is positioned at the same axial position as the recess 202" of the top housing section 200". The spacer member 400" assumes an initial proximal position. The inwards protrusion 233*a*" of the biasing means 233" may abut the spacer member 400" but does not cause the deflectable arm 392" to move outwards. The outwards protrusion 233*b*" is located at an axial position where cooperation with the deflectable arm 392" is potentially possible.

Figure 11B:
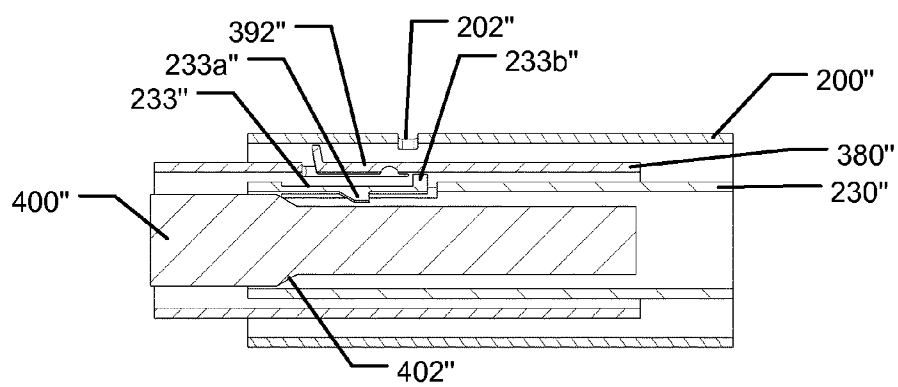

In FIG. 11*b* the needle shield has been moved proximally to trigger the device and the trigger element 380" assumes its proximal position. Hereby, the proximal end of the deflectable arm 392" has been moved axially away from the recess 202". In this state no radial force acts on the deflectable arm 392".

Figure 11C:
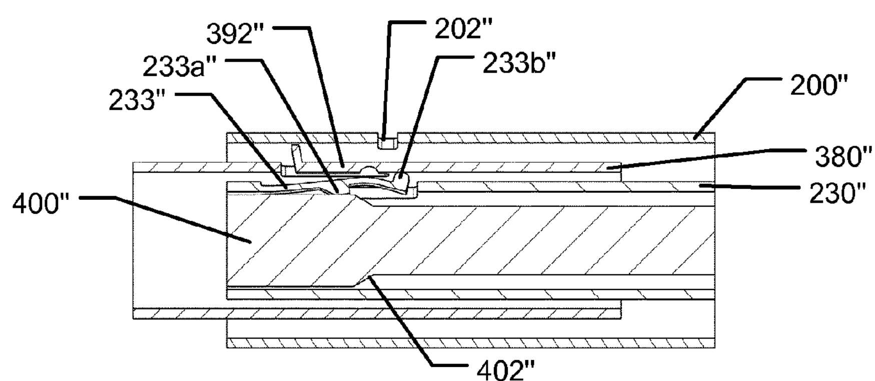
Figure 11D:
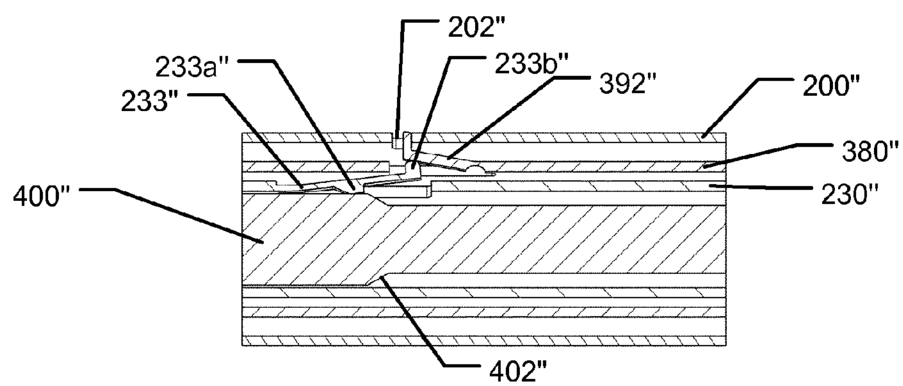

Proximal movement of the trigger element 380' in the state shown in FIG. 11*b* has caused the triggering of the device for initiating the expelling operation. This releases the spacer member 400" to move distally towards the end of dose position which is shown in FIG. 11*c*. Accordingly, the lock activator 402" has moved distally to enter into a distal position. The movement of lock activator 402" has aligned the lock activator 402" into an axial position where it cooperates with the inwards protrusion 233*a*" so that an activation force acts on the biasing means 233" urging the biasing means outwards. As the proximal end of the biasing means 233" is radially non-movable, the distal end of the biasing means is urged outwards. However, as shown in FIG. 11*c*, the outwards protrusion 233*b*" is prevented from moving radially outwards as it abuts an internal surface of the trigger element 380" which radially retains the distal end of the biasing means 233". As a consequence, the biasing means 233" is strained into a curved shape which is maintained until the trigger element 380" is moved into its distal position.

Subsequently to the spacer member 400" having reached the end of dose position as shown in FIG. 11*c*, the device may be withdrawn from the injection site. This moves the trigger element 380" towards its distal position again, see FIG. 11*d*. The proximal end of the deflectable arm 392" has been returned to its initial axial position aligned at an axial position with respect to the recess 202" of the top housing section 200". Due to the strained state of the biasing means 233", the activation force of the lock activator 402" that acts on the biasing means 233" causes the distal end of the deflectable arm 392" to be forced radially outwards and into locking engagement with the recess 202" of the top housing section 200". In this state, the needle shield will be permanently prevented from moving in the proximal direction and thus become finally locked.

In accordance with the functionality of the needle shield lock described for injection device 100, the same overall functionality applies to the needle shield lock according to the first alternative embodiment which has been described in connection with FIGS. 10*a*-10*d* and the needle shield lock according to the second alternative embodiment which has been described in connection with FIGS. 11*a*-11*d*. During the expelling procedure, and before the lock activator assume an axial position in vicinity of a distal end position, should the user prematurely withdraw the injection device from the injection site, the needle shield spring will cause the needle shield to extend into its distal extended position. However, the needle shield will only lock subject to the lock activator assuming an axial position in vicinity of a distal end position, i.e. in the end of dose state where a major portion of the drug has been expelled.

As described above, the deflectable lock element is arranged for being moved in the radial direction between a passive position and into an active position. Also, the biasing means is configured to provide a resiliency in the radial direction for resiliently transferring the activation force from the lock activator towards deflectable lock element.

In alternative not shown embodiments, but still in agreement with the principles set forth above for the needle shield lock mechanism, the deflectable lock element may be configured for being moved in a circumferential direction between a passive (non-locked) position and into an active (locked) position where the deflectable lock element locks relative to the housing of the device. In such embodiments, the lock activator may be configured so that it exerts a torsional activation force on the deflectable lock element subject to the spacer member or plunger having reached its end of dose position. In such embodiments, biasing means may be arranged between the lock activator and the deflectable lock element and configured to provide resiliency in the circumferential direction for resiliently transferring a torsional activation force from the lock activator towards the deflectable lock element. This causes the deflectable lock element to be moved into its active position as the needle shield is moved into its distal extended position.

Some preferred embodiments have been shown in the foregoing, but it should be stressed that the invention is not limited to these, but may be embodied in other ways within the subject matter defined in the following claims.

The invention claimed is:

1. An injection device for expelling a dose of drug from a held cartridge, the injection device comprising:

- a base,
- a drug cartridge arranged relative to the base, the cartridge comprising:
  - an elongated body having a distal end and a proximal end and defining a central longitudinal axis, the body having a distally arranged outlet adapted for connection to a needle, and
  - a piston accommodated in the body, the piston configured for being driven axially in the distal direction to expel a dose of a drug through the outlet, a plunger adapted for cooperation with the piston and driveable towards a final position, and a needle shield axially movable relative to the base between a proximal collapsed position and a distal extended position, wherein the injection device defines a needle shield lock so configured that, when the plunger assumes the final position and when the needle shield assumes the distal extended position, the needle shield lock prevents the needle shield from being moved towards the proximal collapsed position, wherein the needle shield lock comprises a deflectable lock element movable from a passive position wherein the deflectable lock element does not prevent the needle shield from being moved towards the proximal collapsed position and into an active position wherein the deflectable lock element prevents the needle shield from being moved towards the proximal collapsed position, wherein the plunger comprises a lock activator configured for operating the deflectable lock element and being so configured that, when the plunger assumes the final position, the lock activator exerts an activation force on the deflectable lock element for urging the deflectable lock element towards the active position, and wherein a biasing structure is arranged to act between the lock activator and the deflectable lock element, the biasing structure being configured to resiliently transfer the activation force from the lock activator to the deflectable lock element for causing the deflectable lock element to be moved into its active position as the needle shield is moved into its distal extended position.

2. An injection device as defined in claim 1, wherein at least one of the lock activator and the deflectable lock element comprise said biasing structure for resiliently transferring said activation force, the biasing structure being configured for causing the deflectable lock element to be moved into its active position as the needle shield is moved into its distal extended position.

3. An injection device as defined in claim 1, wherein the deflectable lock element moves in a first direction when moving from the passive position to the active position and wherein the biasing structure is configured for providing resiliency along the first direction for resiliently transferring said activation force from the lock activator.

4. An injection device as defined in claim 1, wherein the deflectable lock element assumes the passive position when not being exerted to said activation force by the lock activator.

5. An injection device as defined in claim 1, wherein the base comprises a retaining geometry having a distally facing surface configured for cooperating with a proximally facing surface of the deflectable lock element to prevent the needle shield from moving in the proximal direction when the deflectable lock element assumes the active position.

6. An injection device as defined in claim 1, wherein the deflectable lock element comprises a deflectable arm wherein at least a part of the deflectable arm is configured for moving radially from the passive to the active position.

7. An injection device as defined in claim 5, wherein the deflectable lock element defines an elongated rigid beam having a proximal end that is configured for cooperating with the retaining geometry and having a distal end that connects to the needle shield by way of a hinge so that the proximal end of the elongated rigid beam is movable in a radial direction from the passive position to the active position.

8. An injection device as defined in claim 7, wherein the hinge is a living hinge defined by a component of the needle shield.

9. An injection device as defined in claim 7, wherein, when the deflectable lock element assumes the active position, the elongated rigid beam extends along an axis having an inclination relative to the central longitudinal axis being less than 30 degrees.

10. An injection device as defined in claim 7, wherein the proximal end of the elongated rigid beam comprises a proximally facing surface configured to cooperate with a distally facing surface of the retaining geometry, wherein the proximally facing surface and/or the distally facing surface is inclined with respect to a normal to the central longitudinal axis so that the deflectable lock element, when assuming the active position, is increasingly urged in said radial direction upon increasing force acting in the proximal direction on the needle shield.

11. An injection device as defined in claim 1, wherein a needle shield spring is arranged acting to bias the needle shield towards the extended position.

12. An injection device as defined in claim 1, wherein the needle shield shields a held needle when the needle shield assumes its distal extended position.

13. An injection device as defined in claim 1, wherein the injection device further comprises an actuator for providing a force and arranged to act on the plunger, wherein the actuator is triggerable to drive the piston distally.

14. An injection device as defined in claim 1, wherein the biasing structure moves axially with the plunger.

15. An injection device as defined in claim 1, wherein the biasing structure is formed integrally with the lock activator.

16. An injection device as defined in claim 9, wherein the elongated rigid beam extends along an axis having an inclination relative to the central longitudinal axis being less than 20 degrees.

17. An injection device as defined in claim 9, wherein the elongated rigid beam extends along an axis having an inclination relative to the central longitudinal axis being less than 10 degrees.

* * * * *